(12) United States Patent
Epshtein

(10) Patent No.: US 9,561,273 B2
(45) Date of Patent: Feb. 7, 2017

(54) METHODS OF TREATING MULTIPLE SCLEROSIS

(71) Applicant: Oleg Iliich Epshtein, Moscow (RU)

(72) Inventor: Oleg Iliich Epshtein, Moscow (RU)

(73) Assignee: Oleg Iliich Epshtein, Moscow (RU)

( * ) Notice: Subject to any disclaimer, the term of this patent is extended or adjusted under 35 U.S.C. 154(b) by 57 days.

(21) Appl. No.: 14/048,299

(22) Filed: Oct. 8, 2013

(65) Prior Publication Data

US 2014/0112934 A1    Apr. 24, 2014

Related U.S. Application Data

(62) Division of application No. 13/135,881, filed on Jul. 15, 2011, now Pat. No. 8,637,034.

(30) Foreign Application Priority Data

| Jul. 15, 2010 | (RU) | 2010129296 |
| Jul. 15, 2010 | (RU) | 2010129297 |
| Jul. 27, 2010 | (RU) | 2010131386 |
| Jul. 27, 2010 | (RU) | 2010131387 |
| Jul. 1, 2011 | (RU) | 2011127056 |

(51) Int. Cl.

| A61K 41/00 | (2006.01) |
| A61K 39/395 | (2006.01) |
| A61K 39/00 | (2006.01) |
| C07K 16/18 | (2006.01) |
| C07K 16/24 | (2006.01) |

(52) U.S. Cl.
CPC ....... *A61K 39/3955* (2013.01); *A61K 41/0004* (2013.01); *C07K 16/18* (2013.01); *C07K 16/249* (2013.01); *A61K 2039/505* (2013.01); *A61K 2039/507* (2013.01)

(58) Field of Classification Search
CPC .............. A61K 39/3955; A61K 2039/505; A61K 2039/507; C07K 16/18; C07K 16/249

See application file for complete search history.

(56) References Cited

U.S. PATENT DOCUMENTS

| 3,134,718 | A | 5/1964 | Nobile |
| 3,901,967 | A | 8/1975 | Cohen et al. |
| 4,963,367 | A | 10/1990 | Ecanow |
| 5,683,712 | A | 11/1997 | Cavazza |
| 5,846,514 | A | 12/1998 | Foster et al. |
| 5,849,528 | A | 12/1998 | Hillman et al. |
| 6,150,500 | A | 11/2000 | Salerno |
| 6,750,197 | B1 | 6/2004 | Salerno |
| 7,582,294 | B2 | 9/2009 | Epshtein et al. |
| 7,700,096 | B2 | 4/2010 | Epshtein et al. |
| 7,815,904 | B2 | 10/2010 | Epshtein et al. |
| 7,923,009 | B2 | 4/2011 | Epshtein et al. |
| 8,168,182 | B2 | 5/2012 | Epshtein |
| 8,178,498 | B1 | 5/2012 | Ephstein |
| 8,241,625 | B2 | 8/2012 | Epshtein et al. |
| 8,524,229 | B2 | 9/2013 | Epshtein et al. |
| 8,535,664 | B2 | 9/2013 | Epshtein et al. |
| 8,617,555 | B2 | 12/2013 | Epshtein |
| 8,637,030 | B2 | 1/2014 | Epshtein |
| 8,637,034 | B2 | 1/2014 | Epshtein |
| 8,703,124 | B2 | 4/2014 | Epshtein et al. |
| 8,795,657 | B2 | 8/2014 | Epshtein |
| 8,815,245 | B2 | 8/2014 | Epshtein |
| 2006/0024307 | A1 | 2/2006 | Epshtein |
| 2006/0153845 | A1 | 7/2006 | Epshtein et al. |
| 2007/0123518 | A1 | 5/2007 | Epshtein |
| 2007/0141058 | A1 | 6/2007 | Iliich et al. |
| 2008/0025985 | A1 | 1/2008 | Iliich et al. |
| 2008/0050360 | A1 | 2/2008 | Iliich et al. |
| 2008/0050392 | A1 | 2/2008 | Iliich et al. |
| 2008/0131440 | A1 | 6/2008 | Epshtein et al. |
| 2009/0148521 | A1 | 6/2009 | Epstehin |
| 2010/0166762 | A1 | 7/2010 | Epshtein |
| 2010/0239569 | A1 | 9/2010 | Epshtein |
| 2011/0008452 | A1 | 1/2011 | Epshtein et al. |
| 2011/0086037 | A1 | 4/2011 | Iliich |
| 2012/0225074 | A1 | 9/2012 | Epshtein et al. |
| 2012/0258146 | A1 | 10/2012 | Epshtein |
| 2012/0263725 | A1 | 10/2012 | Epshtein et al. |

(Continued)

FOREIGN PATENT DOCUMENTS

| CA | 2677244 A1 | 8/2008 |
| EP | 1466622 A1 | 10/2004 |
| RU | 2007989 C1 | 2/1994 |
| RU | 2104032 C1 | 2/1998 |
| RU | 2187334 C2 | 3/2000 |
| RU | 2156621 C1 | 9/2000 |
| RU | 2281784 C1 | 8/2006 |
| WO | 9412213 A1 | 6/1994 |

OTHER PUBLICATIONS

Marenholz, I. et al. S100 proteins in mouse and man: from evolution to function and pathology (including an update of the nomenclature). Biochemical and Biophysical Research Communications, 2004, vol. 322, p. 1111-1122.*

Summons to attend oral proceedings pursuant to Rule 115(1) EPC for corresponding European Patent Application No. 11773542-3-1403, Mar. 18, 2015.*

(Continued)

*Primary Examiner* — Robert Landsman
*Assistant Examiner* — Bruce D Hissong
(74) *Attorney, Agent, or Firm* — Pergament & Cepeda LLP; Edward D. Pergament; Milagros A. Cepeda

(57) ABSTRACT

The present invention relates to combination pharmaceutical composition comprising an activated-potentiated from of an antibody to gamma interferon, and an activated-potentiated form of an antibody to S-100 protein and method of treating multiple sclerosis and other neurodegenerative diseases, as well as the diseases and conditions associated with neuroinfections.

5 Claims, 5 Drawing Sheets

(56) References Cited

U.S. PATENT DOCUMENTS

| | | |
|---|---|---|
| 2012/0263726 A1 | 10/2012 | Epshtein et al. |
| 2012/0294899 A1 | 11/2012 | Epshtein et al. |
| 2012/0321672 A1 | 12/2012 | Epshtein |
| 2013/0017202 A1 | 1/2013 | Epshtein et al. |
| 2013/0045237 A1 | 2/2013 | Epshtein et al. |
| 2013/0058981 A1 | 3/2013 | Epshtein |
| 2013/0058982 A1 | 3/2013 | Epshtein |
| 2013/0064860 A1 | 3/2013 | Epshtein |
| 2013/0171161 A1 | 7/2013 | Epshtein et al. |
| 2013/0189707 A1 | 7/2013 | Epshtein et al. |
| 2013/0224219 A1 | 8/2013 | Epshtein et al. |
| 2013/0302312 A1 | 11/2013 | Epshtein et al. |
| 2013/0303735 A1 | 11/2013 | Epshtein et al. |
| 2013/0315964 A1 | 11/2013 | Epshtein et al. |
| 2013/0336985 A1 | 12/2013 | Epshtein et al. |
| 2014/0010819 A1 | 1/2014 | Epshtein et al. |
| 2014/0056923 A9 | 2/2014 | Epshtein et al. |
| 2014/0112934 A1 | 4/2014 | Epshtein |

OTHER PUBLICATIONS

Behensky, A.A. et al. Afobazole activation of sigma-1 receptors modulates neuronal response to Amyloid-beta(25-35), J. Pharmacology and Experimental Therapeutics, 2013, vol. 347, p. 468-477.*

Maurine, T. Protection by sigma-1 receptor agonists is synergic with donepezil, but not with memantine, in a mouse model of amyloid-induced memory impairments, 2016, vol. 296, p. 270-278.*

Nguyen, L, et al. Role of sigma-1 receptors in neurodegenerative diseases, 2015, vol. 127, p. 17-29.*

Ackermann G.E., et al., "S100A1-Deficient Male Mice Exhibit Increased Exploratory Activity and Reduced Anxiety-Related Responses," Biochimica et Biophysica Acta, 2006, No. 1763, pp. 1307-1319.

Bokhan N.A., et al., "Comparative Efficiency of Proproten-100 during the Therapy of Patients with Alcoholism in the Stage of Therapeutic Remission," Bull Exp Biol Med., 2003, Supplement 1, pp. 171-175.

Bombeiro A.L., et al., "Neurodegeneration and Increased Production of Nitrotyrosine, Nitric Oxide Synthase, IFN-y and S100B Protein in the Spinal Cord of IL-12p40-Deficient Mice Infected with Trypanosoma cruzi," NeuroImmunoModulation, 2010, vol. 17, pp. 67-78.

Davenas E., et al., "Human Basophil Degranulation Triggered by Very Dilute Antiserum Against IgE," Nature, Jun. 30, 1988, vol. 333, pp. 816-818.

Diehl L.A., et al., "Long Lasting Sex-Specific Effects Upon Behavior and S100B Levels After Maternal Separation and Exposure to a Model of Post-Traumatic Stress Disorder in Rats," Brain Research, 2007, No. 1144, pp. 107-116.

Duma S.A., et al., "Tenoten in the Therapy of Patients with Moderate Cognitive Impairment," Bull Exp Biol Med., 2009, vol. 148, Suppl. 1, pp. 353-356.

Epshtein O.I., et al., "Psychotropic Drug Tenoten Activates Mitogen-Activated MAP/ERK Kinase Regulatory Cascade Controlling the Neuroprotective Effects," Bull Exp Biol Med., 2007, vol. 144, No. 3, pp. 319-321.

Ernst, Edzard, "Homeopathy: What Does the "Best" Evidence Tell Us?" MJA, Apr. 19, 2010, vol. 192, No. 8, pp. 458-460.

Hu J., et al., "S100B Induces Neuronal Cell Death Through Nitric Oxide Release from Astrocytes," J. Neurochem., 1997, vol. 69, pp. 2294-2301.

Hyman B.T., et al., "National Institute on Aging—Alzheimer's Association Guidelines for the Neuropathologic Assessment of Alzheimer's Disease," Alzheimer's & Dementia, 2012, vol. 8, pp. 1-13.

Linde K., et al., "Are the Clinical Effects of Homoeopathy Placebo Effects? A Meta-Analysis of Placebo-Controlled Trials," The Lancet, 1997, vol. 350, pp. 834-843.

Linde K., et al., "Impact of Study Quality on Outcome in Placebo-Controlled Trials of Homeopathy," J Clin Epidemiol, 1999, vol. 52, No. 7, pp. 631-636.

Romanova G.A., et al., "Neuroprotective Activity of Proproten in Rats with Experimental Local Photothrombosis of the Prefrontal Cortex," Bull Exp Biol Med., 2005, vol. 139, No. 4, pp. 404-407.

Voronina T.A., et al., "Effect of Ultralow Doses of Antibodies to S-100 Protein in Animals with Impaired Cognitive Function and Disturbed Emotional and Neurological Status under Conditions of Experimental Alzheimer Disease," Bull Exp Biol Med., 2009, vol. 148, Suppl. 1, pp. 533-535.

Wiencken A.E., et al., "Endothelial Nitric Oxide Synthetase (eNOS) in Astrocytes: Another Source of Nitric Oxide in Neocortex," GLIA, 1999, vol. 26, pp. 280-290.

Office Action issued by the United States Patent and Trademark Office on Nov. 2, 2012, for corresponding U.S. Appl. No. 13/135,881.

Office Action issued by the United States Patent and Trademark Office on Jul. 26, 2012, for corresponding U.S. Appl. No. 13/135,881.

Vyatcheslav, et al., "Antibodies to Calcium-Binding S100B Protein Block the Conditioning of Long-Term Sensitization in the Terrestrial Snail", Pharmacol Biochem Behav., 2009, vol. 94, No. 1, pp. 37-42.

Schwab V., "Homeopathic Pharmaceutical Agents. A Manual on Description and Preparation," Moscow, 1967, pp. 12-38.

Raine C. S., et al., "Experimental Autoimmune Demyelination, Chronic Relapsing Models and Their Therapeutic Implications for Multiple Sclerosis," Ann. NY Acad. Sci., 1984, vol. 436, pp. 33-51.

Frimel G., "Immunological Methods", 1987, Moscow, Medicina Publishing House, pp. 9-33.

Laffly, et al., "Monoclonal and Recombinant Antibodies, 30 Years After," Human Antibodies, 2005, vol. 14, No. 1-2, pp. 33-55.

McCombe P.A., et al., "Inflammatory Cells, Microglia and MHC Class II Antigen-Positive Cells in the Spinal Cord of Lewis Rats with Acute and Chronic Relapsing Experimental Autoimmune Encephalomyelitis," J Neuroimmunol., 1994, vol. 51, No. 2, pp. 153-167.

Baumann, et al., "Biology of 01 ligodendrocyte and Myelin in the Mammalian Central Nervous System," Physiol. Rev., 2001, vol. 81, No. 2, pp. 871-927.

Stevens, et al., "Oligodendrocyte-Specific Protein Peptides Induce Experimental Autoimmune Encephalomyelitis in SJL/J Mice," J Immunol., 1999, vol. 162, No. 12, pp. 7501-7509.

Online catalog entry for the drug ANAFERON, download Sep. 4, 2013, www.materiamedica.ru/catalogue/detail/?item_id=25&lang=en&for_printing=1.

Skurkovich S., et al."Randomized Study of Antibodies to IFN-y and TNG-a in Secondary Progressive Multiple Sclerosis", Multiple Sclerosis, 2001, vol. 7, pp. 277-284.

Yardan, et al., Usefulness of S100B Protein in Neurological Disorders:, J Pak Med. Assoc., Mar. 2011, vol. 61, No. 3, pp. 276-281.

Kirkby R et al: 'Homeopathic trial design in influenza treatment', Homeopathy, Churchill Livingstone, Amsterdam, NL, vol. 99, No. 1, Jan. 1, 2010, pp. 69-75, XP026988523, ISSN: 1475-4916 [retrieved on Jan. 15, 2010).

Beregovoi N A et al: Effect of antibodies to morphine in ultralow doses on induction of long-term potentiation in hippocampal slices from rats with chronic morphine dependence., Bulletin of Experimental Biology and Medicine Jan. 2003, vol. 135 Suppl 7, Jan. 2003, pp. 26.28, ISSN: 1573-8221.

Dugina J L et al: "A randomized, open-label, comparative, 6-month trial of oral ultra-low doses of antibodies to tumor necrosis factor-alpha and diclofenac in rheumatoid arthritis.", International Journal of Tissue Reactions 2005, vol. 27, No. 1, 2005, pp. 15-21, ISSN: 0250-0868.

Epstein 0 I et al: "Dose-dependent effects and specificity of action of antibodies to endogenous regulators in ultralow doses.", Bulletin of Experimental Biology and Medicine May 2004, vol. 137, No. 5, May 2004, pp. 460-462, ISSN: 0007-4888.

(56) References Cited

OTHER PUBLICATIONS

Epstein 0 1 et al: "Improvement of Memory by Means of Ultra-Low Doses of Antibodies to S-100B Antigen.", Evidence-Based Complementary and Alternative Medicine : ECAM Dec. 2006, vol. 3, No. 4, Dec. 2006, pp. 541-545, ISSN: 1741-427X.

Krylova S G et al: "Antiulcer activity of ultralow doses of antibodies to histamine under experimental conditions.", Bulletin of Experimental Biology and Medicine Jan. 2003, vol. 135 Suppl 7, Jan. 2003, pp. 80-82, ISSN: 1573-8221.

Markel' A L et al: Hypotensive activity of ultralow doses of antibodies to factors involved in the regulation of vascular tone., Bulletin of Experimental Biology and Medicine Jan. 2003, vol. 135 Suppl 7, Jan. 2003, pp. 57-59, ISSN: 1573-8221.

Voronova 0 L et al: "Cytogenetic effects of antibodies to gamma-interferon in ultralow doses.", Bulletin of Experimental Biology and Medicine Jan. 2003, vol. 135 Suppl 7, Jan. 2003, pp. 65-66, ISSN: 1573-8221.

Spasov A A et al: "Study of antidiabetic activity of a new ultralow-dose antibody preparation on the model of streptozotocin diabetes in rats.", Bulletin of Experimental Biology and Medicine Jul. 2007, vol. 144, No. 1, Jul. 2007, pp. 46-48, ISSN: 0007-4888.

Montagnier Luc: "Newsmaker interview: Luc Montagnier. French Nobelist escapes 'intellectual terror' to pursue radical ideas in China. Interview by Martin Enserink.", Science (New York, N.Y.) Dec. 24, 2010, vol. 330, No. 6012, Dec. 24, 2010, p. 1732, ISSN: 1095-9203.

Linde K et al: Are the clinical effects of homeopathy placebo effects? A meta-analysis of placebo-controlled trials., Lancet Sep. 20, 1997, vol. 350, No. 9081, Sep. 20, 1997, pp. 834-843, ISSN: 0140-6736.

Abstract of Weerth et al., "Encephalitogenic and neuritogenic T cell responses to the myelin-associated glycoprotein (MAG) in the Lewis rat", Journal of Neuroimmunology, Mar. 1, 1999, pp. 157-164, vol. 95-issue No. 1-2.

Abstract of VK Tuohy, "Peptide determinants of myelin proteolipid protein (PLP) in autoimmune demyelinating disease: a review", Neurochem Res., Aug. 1994, pp. 935 to 944, vol. 19-issue No. 6.

Abstract of Gilerovich et al., "Analysis of morphological manifestations of the inflammatory reaction in wistar rat spinal cord in experimental model", Morfologiia, 2010, pp. 16-20, vol. 137-issue No. 5.

Abstarct of Bradl and Linington, "Animal models of demyelination", Brain Pathol., Jul. 1996, pp. 303-311, vol. 6-issue No. 3.

Voronina et al., "Antibodies to S-100 Protein in Anxiety-Depressive Disorders in Experimental and Clinical conditions", Chapter 8 in Animal Models in Biological Psychiatry, Editor—Allan V. Kalueff, 2006, pp. 137-152, Nova Science Publishers, Inc.

* cited by examiner

METHODS OF TREATING MULTIPLE SCLEROSIS

This application is a divisional application of U.S. patent application Ser. No. 13/135,881 which was filed on Jul. 15, 2011, now pending, the contents of which is hereby incorporated by reference. This application also claims priority to Russian Federation Application Nos. 2010131387 (filed Jul. 27, 2010), 2011127056 (filed Jul. 1, 2011), 20100131386 (filed Jul. 27, 2010), 2010129296 (Jul. 15, 2010) and 2010129297 (Jul. 15, 2010), the contents of which are hereby incorporated by reference.

FIELD

The present invention relates to a combination pharmaceutical compositions and method of treating multiple sclerosis and other neurodegenerative diseases, as well as the diseases and conditions associated with neuroinfections.

BACKGROUND

Multiple sclerosis or MS is a chronic disease that affects the brain and spinal cord resulting in loss of muscle control, balance, and sensation (such as numbness). Currently, the exact cause of MS remains unknown, but researchers believe that a combination of several factors may be involved. It is believed that MS appears in genetically predisposed individuals possibly in the presence of specific external factors which lead to the development of MS. It is now generally accepted that MS involves an autoimmune process—an abnormal response of the body's immune system that is directed against the myelin (the fatty sheath that surrounds and insulates the nerve fibers) in the central nervous system (CNS—the brain, spinal cord and optic nerves). MS results in a thinning or complete loss of myelin and, as the disease advances, the cutting (transection) of the neuron's extensions or axons. When the myelin is lost, a neuron can no longer effectively conduct electrical signals. A repair process, called remyelination, takes place in early phases of the disease, but the cell's myelin sheath cannot be completely rebuilt. Repeated attacks lead to successively fewer effective remyelinations, until a scar-like plaque is built up around the damaged axons.

Apart from demyelination, the other pathologic trait of the disease is inflammation. According to a strictly immunological explanation, the inflammatory process is caused by T cells, a kind of lymphocyte. Lymphocytes are cells that play an important role in the body's defenses. In MS, T cells gain entry into the brain via the blood-brain barrier. It is believed that the T cells recognize myelin as foreign and attack it which triggers inflammatory processes, stimulating other immune cells and soluble factors like cytokines and antibodies.

In addition to autoimmune disorder, some researchers believe that infections may somehow trigger the immune system to attack nerve cells. Basically, it is believed that the virus (or a bacterium) that causes an initial infection "looks" like a nerve cell. The immune system develops T-cells to fight off the virus. Those T-cells remain in the body after the infection is gone and become confused when they "see" a nerve cell, mistaking it for an invader. The result is that your immune system attacks the nervous system.

There are four main varieties of MS. 1. Relapsing/Remitting (RRMS): characterised by relapses during which time new symptoms can appear and old ones resurface or worsen. 2. Secondary Progressive (SPMS): characterized by a gradual worsening of the disease between relapses. 3. Progressive Relapsing Multiple Sclerosis (PRMS): This form of MS follows a progressive course from onset, punctuated by relapses. 4. Primary Progressive (PPMS): This type of MS is characterized by a gradual progression of the disease from its onset with no remissions at all.

There is no known cure for MS at this time. However, there are therapies that may slow the disease. The goal of treatment is to control symptoms. Medications that alter the immune system, for example interferons, have been used to manage multiple sclerosis. Interferons are protein messengers that cells of the immune system manufacture and use to communicate with one another. There are different types of interferons, such as alpha, beta, and gamma. All interferons have the ability to regulate the immune system and play an important role in protecting against intruders including viruses. Each interferon functions differently, but the functions overlap. The beta interferons have been found useful in managing multiple sclerosis.

There is a continuing need for new drug products with desired therapeutic efficacy for treatment of MS and related symptoms.

The therapeutic effect of an extremely diluted form (or ultra-low form) of antibodies potentized by homeopathic technology (activated potentiated form) has been discovered by the inventor of the present patent application, Dr. Oleg I. Epshtein. U.S. Pat. No. 7,582,294 discloses a medicament for treating Benign Prostatic Hyperplasia or prostatitis by administration of a homeopathically activated form of antibodies to prostate specific antigen (PSA).

The S-100 protein is a cytoplasmic acidic calcium binding protein found predominantly in the gray matter of the brain, primarily in glia and Schwann cells. The protein exists in several homo- or heterodimeric isoforms consisting of two immunologically distinct subunits, alpha and beta. The S-100 protein has been suggested for use as an aid in the diagnosis and assessment of brain lesions and neurological damage due to brain injury, as in stroke. Yardan et al., Usefulness of S100B Protein in Neurological Disorders, J Pak Med Assoc Vol. 61, No. 3, March 2011, which is incorporated herein by reference.

Ultra low doses of antibodies to S-100 protein have been shown to have anxiolytic, anti-asthenic, anti-aggressive, stress-protective, anti-hypoxic, anti-ischemic, neuroprotective and nootropic activity. See Castagne V. et al., *Antibodies to S*100 *proteins have anxiolytic-like activity at ultra-low doses in the adult rat*, J Pharm Pharmacol. 2008, 60(3):309-16; Epstein O. I., *Antibodies to calcium-binding S*1008 *protein block the conditioning of long-term sensitization in the terrestrial snail*, Pharmacol Biochem Behav., 2009, 94(1):37-42; Voronina T. A. et al., Chapter 8. *Antibodies to S-*100 *protein in anxiety-depressive disorders in experimental and clinical conditions. In "Animal models in biological psychiatry"*, Ed. Kalueff A. V. N—Y, "Nova Science Publishers, Inc.", 2006, pp. 137-152, all of which are incorporated herein by reference.

Ultra low doses of antibodies to gamma interferon have been shown to be useful in the treatment and prophylaxis of treating a disease of viral origination. See U.S. Pat. No. 7,572,441, which is incorporated herein by reference in its entirety.

SUMMARY

In one aspect, the invention provides a combination pharmaceutical composition comprising a) an activated-potentiated form of an antibody to gamma interferon, and b) an activated-potentiated form of an antibody to S-100 protein.

In one variant, the present invention provides a combination pharmaceutical composition comprising a) an activated-potentiated form of an antibody to gamma interferon, and b) an activated-potentiated form of an antibody to S-100 protein, wherein the antibody is to the entire gamma interferon or fragments thereof.

In one variant, the invention provides a combination pharmaceutical composition comprising a) an activated-potentiated form of an antibody to gamma interferon, and b) an activated-potentiated form of an antibody to S-100 protein, wherein the antibody to the S-100 protein is an antibody to the entire S-100 protein or fragments thereof.

In one variant, the combination pharmaceutical composition of this aspect of the invention includes activated-potentiated form of an antibody to gamma interferon is in the form of a mixture of (C12, C30, and C50) or (C12, C30 and C200) homeopathic dilutions impregnated onto a solid carrier. The activated-potentiated form of an antibody to S-100 protein is in the form of mixture of (C12, C30, and C50) or (C12, C30 and C200) homeopathic dilutions may be subsequently impregnated onto the solid carrier.

In another variant, the combination pharmaceutical composition of this aspect of the invention includes the activated-potentiated form of an antibody to S-100 protein is in the form of mixture of (C12, C30, and C50) or (C12, C30 and C200) homeopathic dilutions impregnated onto a solid carrier. The activated-potentiated form of an antibody to gamma interferon is in the form of mixture of (C12, C30, and C50) or (C12, C30 and C200) homeopathic dilutions may be subsequently impregnated onto the solid carrier.

Preferably, the activated-potentiated form of an antibody to gamma interferon is a monoclonal, polyclonal or natural antibody, more preferably, a polyclonal antibody. In one variant of this aspect of the invention, the activated-potentiated form of an antibody to gamma interferon is prepared by successive centesimal dilutions coupled with shaking of every dilution.

Preferably, the activated-potentiated form of an antibody to S-100 protein is a monoclonal, polyclonal or natural antibody, more preferably, a polyclonal antibody. In one variant of this aspect of the invention, the activated-potentiated form of an antibody to S-100 protein is prepared by successive centesimal dilutions coupled with shaking of every dilution. Vertical shaking is specifically contemplated.

In another aspect, the invention provides a method of treating a patient suffering from multiple sclerosis by administration of a) an activated-potentiated form of an antibody to gamma interferon, and b) an activated-potentiated form of an antibody to S-100 protein. Preferably, the activated-potentiated form of an antibody to gamma interferon and the activated-potentiated form of an antibody to S-100 protein are administered in the form of combined pharmaceutical composition.

In another aspect, the invention provides a method of significantly delaying the onset of symptoms in a patient suffering from multiple sclerosis by administration of a combination pharmaceutical composition wherein the composition comprises a) an activated-potentiated form of an antibody to gamma interferon, and b) an activated-potentiated form of an antibody to S-100 protein.

In another aspect, the present invention further provides a method of reducing the frequency of appearance of relapse in a patient suffering from multiple sclerosis by administration of a combination pharmaceutical composition wherein the composition comprises a) an activated-potentiated form of an antibody to gamma interferon, and b) an activated-potentiated form of an antibody to S-100 protein.

In one variant of the invention, there is provided administration of from one to two unit dosage forms of the activated-potentiated form of an antibody to gamma interferon, and from one to two unit dosage forms of the activated-potentiated form of an antibody to S-100 protein each of the dosage form being administered from once daily to four times daily. Preferably, the one to two unit dosage forms of each of the activated-potentiated forms of antibodies is administered twice daily.

In a preferred variant of this aspect of the invention, there is provided administration of from one to two unit dosage forms, of the combination composition comprising a) the activated-potentiated form of an antibody to gamma interferon, and b) the activated-potentiated form of an antibody to S-100 protein, each of the dosage form being administered from once daily to four times daily. Preferably, one to two unit dosage forms are administered twice daily.

In another variant of this aspect of the invention, which is preferred, the combination is administered in the form of one unit dosage form comprising a) the activated-potentiated form of an antibody to gamma interferon, and b) the activated-potentiated form of an antibody to S-100 protein, preferably twice daily.

DETAILED DESCRIPTION

Figure 1:
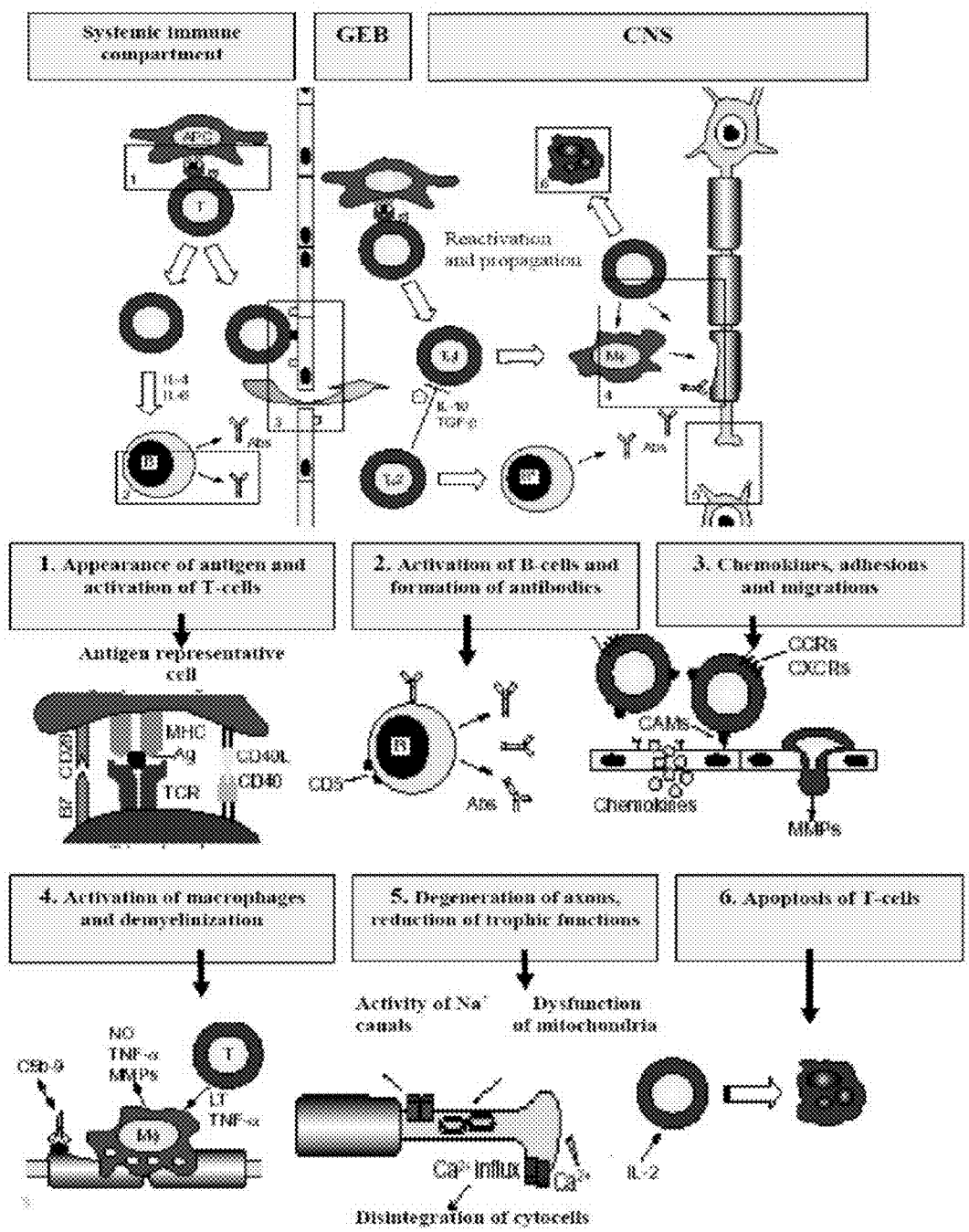
FIG. 1—Illustrates the immune response in pathogenesis of multiple sclerosis
Figure 2:
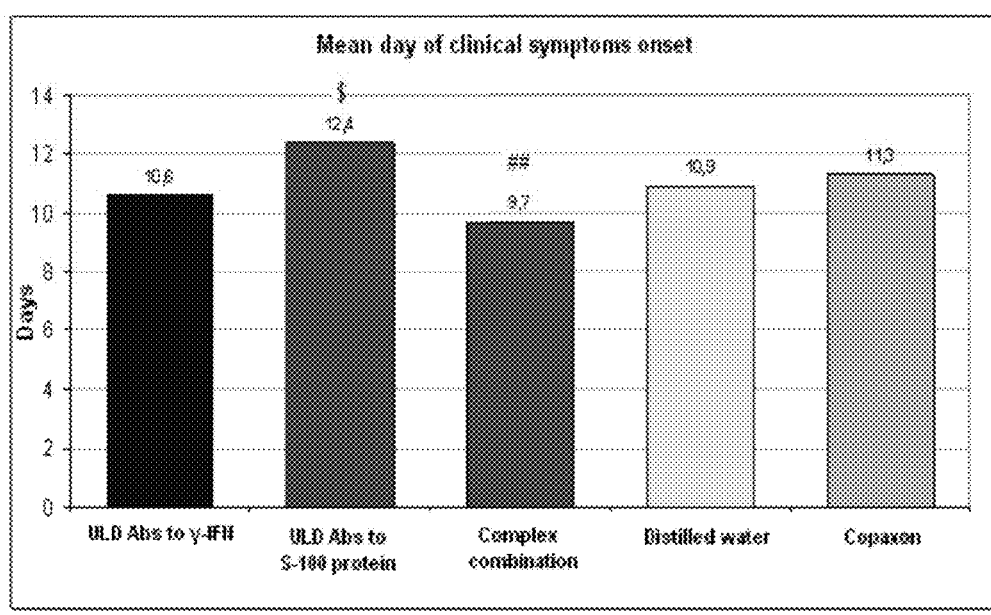
FIG. 2—Shows the mean day of clinical symptoms onset
Figure 3:
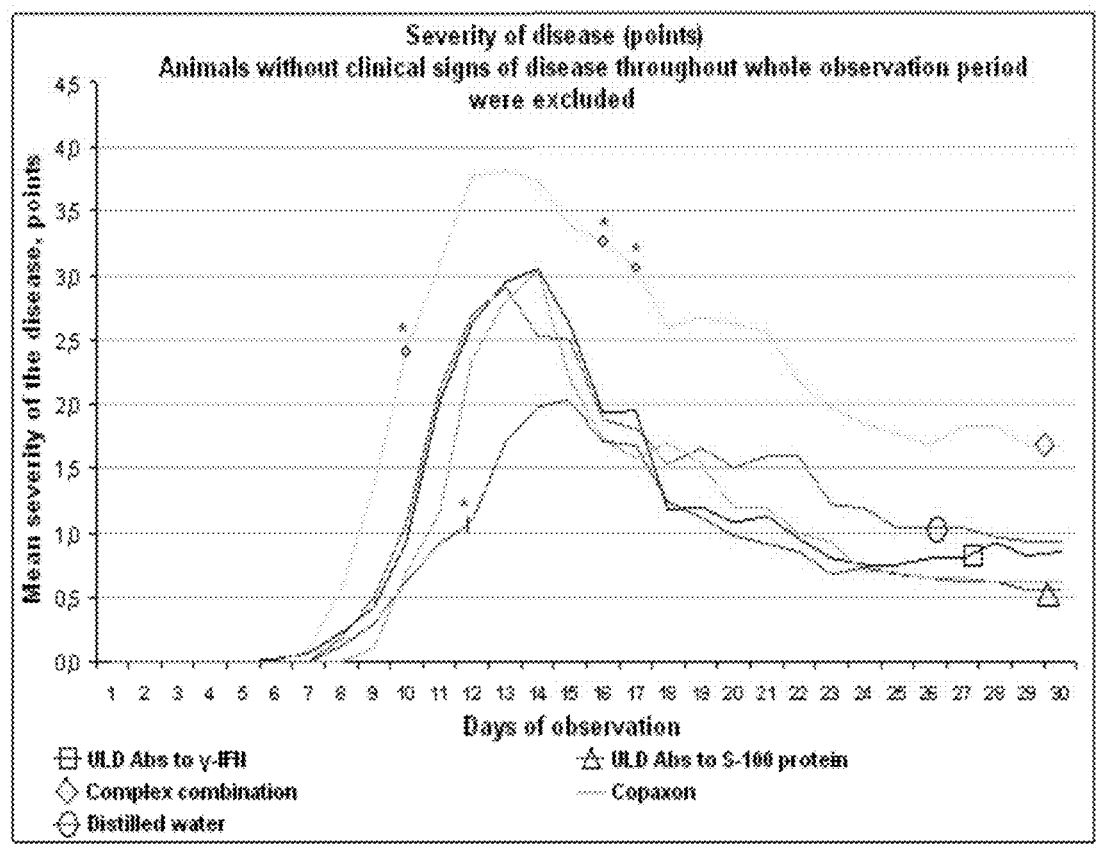
FIG. 3—Shows the severity of disease (points)
Figure 4:
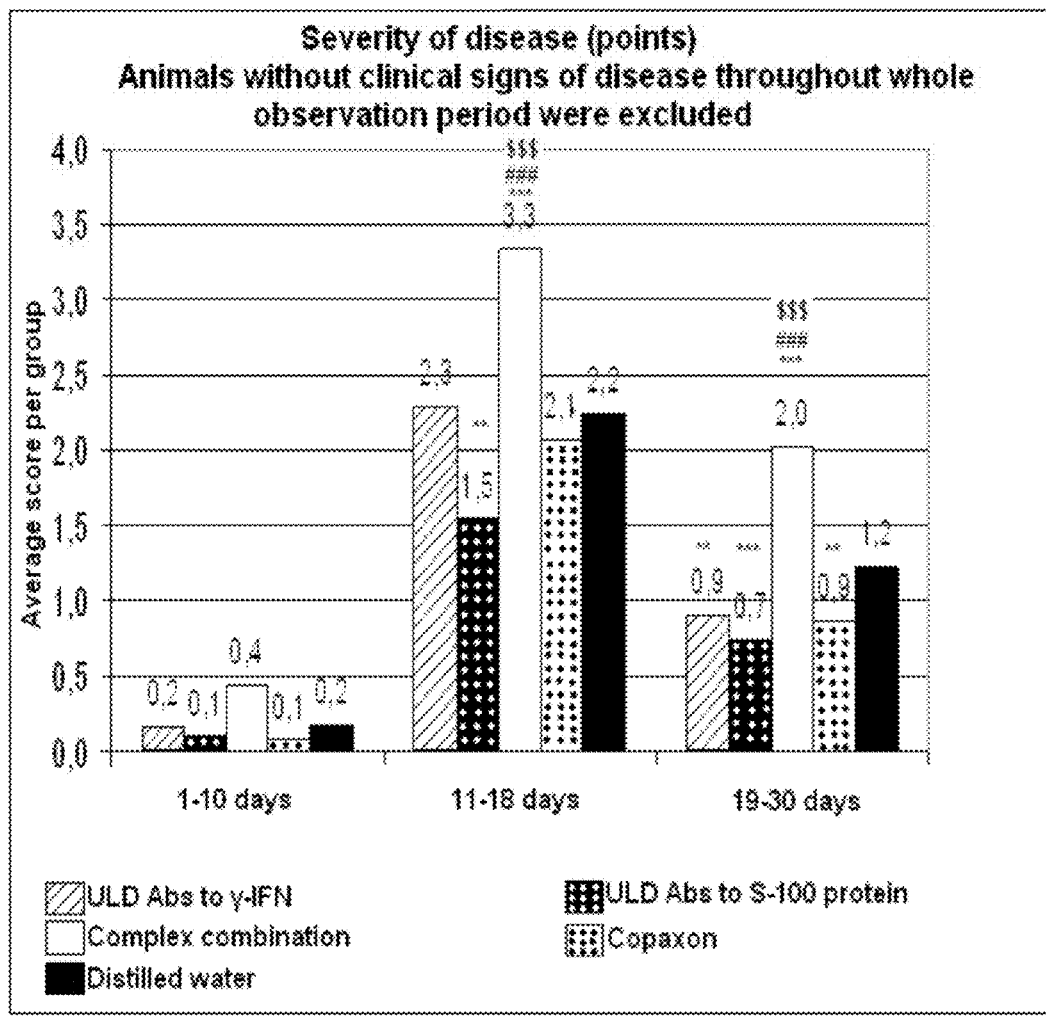
FIG. 4—Shows the severity of disease at different stages (points)
Figure 5:
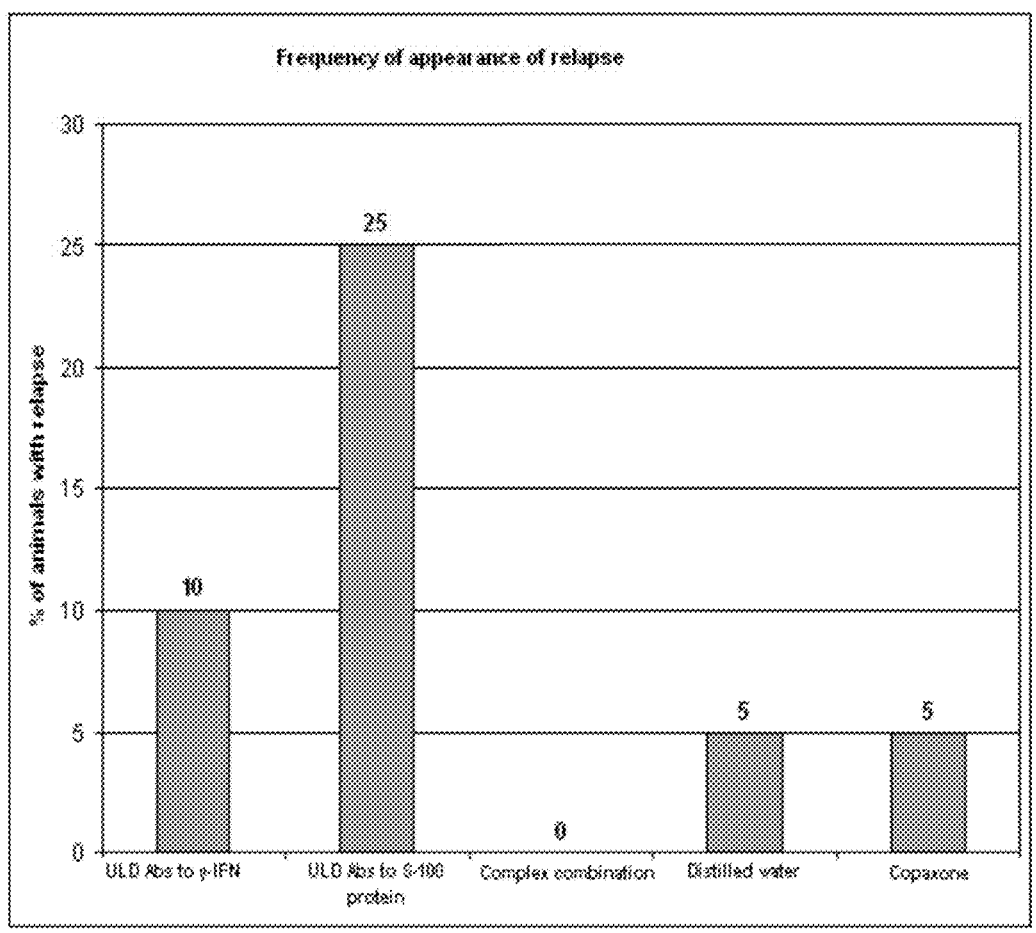
FIG. 5—Shows the frequency of appearance of relapse

The invention is defined with reference to the appended claims. With respect to the claims, the glossary that follows provides the relevant definitions.

The term "antibody" as used herein shall mean an immunoglobulin that specifically binds to, and is thereby defined as complementary with, a particular spatial and polar organization of another molecule. Antibodies as recited in the claims may include a complete immunoglobulin or fragment thereof, may be natural, polyclonal or monoclonal, and may include various classes and isotypes, such as IgA, IgD, IgE, IgG1, IgG2a, IgG2b and IgG3, IgM, etc. Fragments thereof may include Fab, Fv and F(ab')$_2$, Fab', and the like. The singular "antibody" includes plural "antibodies".

The term "activated-potentiated form" or "potentiated form" respectively, with respect to antibodies recited herein is used to denote a product of homeopathic potentization of any initial solution of antibodies. "Homeopathic potentization" denotes the use of methods of homeopathy to impart homeopathic potency to an initial solution of relevant substance. Although not so limited, 'homeopathic potentization" may involve, for example, repeated consecutive dilutions combined with external treatment, particularly (mechanical) shaking. In other words, an initial solution of antibody is subjected to consecutive repeated dilution and multiple vertical shaking of each obtained solution in accordance with homeopathic technology. The preferred concentration of the initial solution of antibody in the solvent, preferably water or a water-ethyl alcohol mixture, ranges from about 0.5 to about 5.0 mg/ml. The preferred procedure for preparing each component, i.e. antibody solution, is the use of the mixture of three aqueous or aqueous-alcohol dilutions of the primary matrix solution (mother tincture) of antibodies diluted $100^{12}$, $100^{30}$ and $100^{200}$ times, respectively, which is equivalent to centesimal homeopathic dilutions (C12, C30, and C200) or the use of the mixture of three aqueous or aqueous-alcohol dilutions of the primary matrix solution of antibodies diluted $100^{12}$, $100^{30}$ and $100^{50}$ times, respectively, which is equivalent to centesimal homeopathic dilutions (C12, C30 and C50). Examples of homeopathic potentization are described in U.S. Pat. Nos. 7,572,441 and 7,582,294, which are incorporated herein by reference in their entirety and for the purpose stated. While the term "activated-potentiated form" is used in the claims, the term "ultra-low doses" is used in the examples. The term "ultra-low doses" became a term of art in the field of art created by study and use of homeopathically diluted and potentized form of substance. The term "ultra-low dose" or "ultra-low doses" is meant as fully supportive and primarily synonymous with the term 'activated-potentiated" form used in the claims.

In other words, an antibody is in the "activated-potentiated" or "potentiated" form when three factors are present. First, the "activated-potentiated" form of the antibody is a product of a preparation process well accepted in the homeopathic art. Second, the "activated-potentiated" form of antibody must have biological activity determined by methods well accepted in modern pharmacology. And third, the biological activity exhibited by the "activated potentiated" form of the antibody cannot be explained by the presence of the molecular form of the antibody in the final product of the homeopathic process.

For example, the activated potentiated form of antibodies may be prepared by subjecting an initial, isolated antibody in a molecular form to consecutive multiple dilutions coupled with an external impact, such as mechanical shaking. The external treatment in the course of concentration reduction may also be accomplished, for example, by exposure to ultrasonic, electromagnetic, or other physical factors. V. Schwabe "Homeopathic medicines", M., 1967, U.S. Pat. Nos. 7,229,648 and 4,311,897, which are incorporated by reference in their entirety and for the purpose stated, describe such processes that are well accepted methods of homeopathic potentiation in the homeopathic art. This procedure gives rise to a uniform decrease in molecular concentration of the initial molecular form of the antibody. This procedure is repeated until the desired homeopathic potency is obtained. For the individual antibody, the required homeopathic potency can be determined by subjecting the intermediate dilutions to biological testing in the desired pharmacological model. Although not so limited, 'homeopathic potentization" may involve, for example, repeated consecutive dilutions combined with external treatment, particularly vertical (mechanical) shaking. In other words, an initial solution of antibody is subjected to consecutive repeated dilution and multiple vertical shaking of each obtained solution in accordance with homeopathic technology. The preferred concentration of the initial solution of antibody in the solvent, preferably, water or a water-ethyl alcohol mixture, ranges from about 0.5 to about 5.0 mg/ml. The preferred procedure for preparing each component, i.e. antibody solution, is the use of the mixture of three aqueous or aqueous-alcohol dilutions of the primary matrix solution (mother tincture) of antibodies diluted $100^{12}$, $100^{30}$ and $100^{200}$ times, respectively, which is equivalent to centesimal homeopathic dilutions C12, C30 and C200 or the mixture of three aqueous or aqueous-alcohol dilutions of the primary matrix solution (mother tincture) of antibodies diluted $100^{12}$, $100^{30}$ and $100^{50}$ times, respectively, which is equivalent to centesimal homeopathic dilutions C12, C30 and C50. Examples of how to obtain the desired potency are also provided, for example, in U.S. Pat. Nos. 7,229,648 and 4,311,897, which are incorporated by reference for the purpose stated. The procedure applicable to the "activated potentiated" form of the antibodies described herein is described in more detail below.

There has been a considerable amount of controversy regarding homeopathic treatment of human subjects. While the present invention relies on accepted homeopathic processes to obtain the "activated-potentiated" form of antibodies, it does not rely solely on homeopathy in human subjects for evidence of activity. It has been surprisingly discovered by the inventor of the present application and amply demonstrated in the accepted pharmacological models that the solvent ultimately obtained from consecutive multiple dilution of a starting molecular form of an antibody has definitive activity unrelated to the presence of the traces of the molecular form of the antibody in the target dilution. The "activated-potentiated" form of the antibody provided herein are tested for biological activity in well accepted pharmacological models of activity, either in appropriate in vitro experiments, or in vivo in suitable animal models. The experiments provided further below provide evidence of biological activity in such models. Human clinical studies also provide evidence that the activity observed in the animal model is well translated to human therapy. Human studies have also provided evidence of availability of the "activated potentiated" forms described herein to treat specified human diseases or disorders well accepted as pathological conditions in the medical science.

Also, the claimed "activated-potentiated" form of antibody encompasses only solutions or solid preparations the biological activity of which cannot be explained by the presence of the molecular form of the antibody remaining from the initial, starting solution. In other words, while it is contemplated that the "activated-potentiated" form of the antibody may contain traces of the initial molecular form of the antibody, one skilled in the art could not attribute the observed biological activity in the accepted pharmacological models to the remaining molecular form of the antibody with any degree of plausibility due to the extremely low concentrations of the molecular form of the antibody remaining after the consecutive dilutions. While the invention is not limited by any specific theory, the biological activity of the "activated-potentiated' form of the antibodies of the present invention is not attributable to the initial molecular form of the antibody. Preferred is the "activated-potentiated" form of antibody in liquid or solid form in which the concentration of the initial molecular form of the antibody is below the limit of detection of the accepted analytical techniques, such as capillary electrophoresis and High Performance Liquid Chromatography. Particularly preferred is the "activated-potentiated" form of antibody in liquid or solid form in which the concentration of the initial molecular form of the antibody is below the Avogadro number. In the pharmacology of molecular forms of therapeutic substances, it is common practice to create a dose-response curve in which the level of pharmacological response is plotted against the concentration of the active drug administered to the subject or tested in vitro. The minimal level of the drug which produces any detectable response is known as a threshold dose. It is specifically contemplated and preferred that the "activated-potentiated" form of the antibodies contains molecular antibody, if any, at a concentration below the threshold dose for the molecular form of the antibody in the given biological model.

Experimental animal models of multiple sclerosis are known. For example, Experimental autoimmune encephalomyelitis, sometimes Experimental Allergic Encephalomyelitis (EAE) is an animal model of inflammatory demyelinating diseases of the central nervous system. It is mostly used with rodents and knockout mice. This experimental model is widely studied as an animal model of the human central nervous system demyelinating diseases, such as multiple sclerosis. It is possible to induce EAE in sensory animals by homogenate of homologous or heterologous cerebral tissue, purified myelin or proteins being introduced into the animal's composition (Raine, et al., Ann. NY Acad. Sci., 1984, 436: 33-51; McCombe, et al., J. Neuroimmunol. 1994; 51 (2): 153-167).

At the present time, more than 20 myelin proteins have been described which possess immunogenic properties and most frequently are used for inducting EAE (Baumann, et al., Physiol. Rev. 2001, 81(2): 871-927). Examples include: basic myelin protein ("MBP") (Hashim, Immunol. Rev., 1978, 39:60-107); proteolipid protein ("PLP") (Bradt, et al., Brain Pathol., 1996, 6(3): 303-311; Tuohy, Neurochem. Res., 1994, 19(8): 935-944); glycoproteins: myelin associated glycoprotein ("MAG") (Weerth et al, 1999); myelin oligodendrocyte glycoprotein ("MOG"); and oligodendrocyte specific protein ("OSP") (Stevens, et al., J. Immunol., 1999; 162 (12): 7501-7509). It is recognized that, not only whole proteins, but also specific fragments of these proteins are capable of causing EAE when introduced into animals. The most commonly used antigens in rodents are spinal cord homogenate (SCH), purified myelin, myelin protein such as MBP, PLP and MOG or peptides of these proteins, all resulting in distinct models with different disease characteristics regarding both immunology and pathology.

The most adequate model MS is caused in EAE models by introducing homogenate of spinal cord (Gilerovich et al, 2010; Zhabotinskiy, Joffe, 1975; Zhitnukhin et al, 2008; Sinha et al, 2009). In this model, as with the initial disease, immune response is made to all components of myelin: inflammation is induced with subsequent demyelination, degeneration of axons and then the nerve cells themselves (Gilerovich et al, 2010; Sinha et al, 2009). A pathologic chain of events is manifested with development of pareses, paralyzes and other disease symptoms.

In the development of EAE, it was possible to distinguish four stages: 1. Sensitization of T-lymphocytes on the periphery under the effect of cerebral antigen with CFA and increase in the permeability of GEB. 2. Migration of activated T-cells to the CNS and activation of antigen-representing cells (astrocytes and microglia) directly in the brain. These two stages correspond to the latent (induction) period when clinical manifestations are not observed. 3. Development of autoimmune and inflammatory reactions in the brain, which leads to demyelination of nerve fibers (clinical period). 4. Suppression of pathologic processes and repair of damaged tissues (recovery phase). During this period, neurologic and motor disorders are smoothed in the majority of animals and partial or complete recovery ensues, after which animals are resistant to the repeated induction of EAE. The average duration of EAE is 30 days: latent stage, clinical stage and recovery stage. The duration of each stage is usually 7-10 days.

Analogous phases of development of the pathologic process in the CNS are also observed with multiple sclerosis. See FIG. 1—Immune response in pathogenesis of multiple sclerosis (Wiendl & Kieseier, 2003).

The present invention provides a combination pharmaceutical composition comprising a) an activated-potentiated form of an antibody to gamma interferon, and b) an activated-potentiated form of an antibody to S-100 protein. As set forth herein above, each of the individual components of the combination is generally known for its own individual medical uses. However, the inventors of the present patent application surprisingly discovered that administration of the combination remarkably delays the onset of symptoms and reduces the probability of relapse in patients with multiple sclerosis.

The combination pharmaceutical composition in accordance with this aspect of the invention may be in the liquid form or in solid form. Each of the activated potentiated forms of the antibodies included in the pharmaceutical composition is prepared from an initial molecular form of the antibody via a process accepted in homeopathic art. The starting antibodies may be monoclonal, or polyclonal antibodies prepared in accordance with known processes, for example, as described in Immunotechniques, G. Frimel, M., "Meditsyna", 1987, p. 9-33; "Hum. Antibodies. Monoclonal and recombinant antibodies, 30 years after" by Laffly E., Sodoyer R. —2005—Vol. 14. —N 1-2. P. 33-55, both incorporated herein by reference.

Monoclonal antibodies may be obtained, e.g., by means of hybridoma technology. The initial stage of the process includes immunization based on the principles already developed in the course of polyclonal antisera preparation. Further stages of work involve the production of hybrid cells generating clones of antibodies with identical specificity. Their separate isolation is performed using the same methods as in the case of polyclonal antisera preparation.

Polyclonal antibodies may be obtained via active immunization of animals. For this purpose, for example, suitable animals (e.g. rabbits) receive a series of injections of the appropriate antigen, either S-100 protein or gamma interferon. The animals' immune system generates corresponding antibodies, which are collected from the animals in a known manner. This procedure enables preparation of a monospecific antibody-rich serum.

If desired, the serum containing antibodies may be purified, for example by using affine chromatography, fractionation by salt precipitation, or ion-exchange chromatography. The resulting purified, antibody-enriched serum may be used as a starting material for the preparation of the activated-potentiated form of the antibodies. The preferred concentration of the resulting initial solution of antibody in the solvent, preferably water or a water-ethyl alcohol mixture, ranges from about 0.5 to about 5.0 mg/ml.

The preferred procedure for preparing each component of the combination drug according to the present invention is the use of the mixture of three aqueous-alcohol dilutions of the primary matrix solution of antibodies diluted $100^{12}$, $100^{30}$ and $100^{50}$ times, respectively, which is equivalent to centesimal homeopathic dilutions C12, C30, and C50 or diluted $100^{12}$, $100^{30}$ and $100^{200}$ times, respectively, which is equivalent to centesimal homeopathic dilutions C12, C30 and C200. To prepare a solid dosage form, a solid carrier is treated with the desired dilution obtained via the homeopathic process. To obtain a solid unit dosage form of the combination of the invention, the carrier mass is impregnated with each of the dilutions. Both orders of impregnation are suitable to prepare the desired combination dosage form.

In a preferred embodiment, the starting material for the preparation of the activated potentiated form that comprise the combination of the invention is polyclonal, animal-raised antibody to the corresponding antigen, namely, gamma interferon or S-100 protein. To obtain the activated-potentiated form of polyclonal antibodies to gamma interferon, the desired antigen may be injected as immunogen into a laboratory animal, preferably, rabbits. Polyclonal antibodies to gamma interferon may be obtained using the whole molecule of gamma interferon of the following sequence:

SEQ. ID. NO. 1.

```
Met Lys Tyr Thr Ser Tyr Ile Leu Ala Phe Gln Leu Cys Ile Val
1               5                   10                  15

Leu Gly Ser Leu Gly Cys Tyr Cys Gln Asp Pro Tyr Val Lys Glu
16              20                  25                  30

Ala Glu Asn Leu Lys Lys Tyr Phe Asn Ala Gly His Ser Asp Val
31              35                  40                  45

Ala Asp Asn Gly Thr Leu Phe Leu Gly Ile Leu Lys Asn Trp Lys
46              50                  55                  60

Glu Glu Ser Asp Arg Lys Ile Met Gln Ser Gln Ile Val Ser Phe
61              65                  70                  75

Tyr Phe Lys Leu Phe Lys Asn Phe Lys Asp Asp Gln Ser Ile Gln
76              80                  85                  90

Lys Ser Val Glu Thr Ile Lys Glu Asp Met Asn Val Lys Phe Phe
91              95                  100                 105

Asn Ser Asn Lys Lys Lys Arg Asp Asp Phe Glu Lys Leu Thr Asn
106             110                 115                 120

Tyr Ser Val Thr Asp Leu Asn Val Gln Arg Lys Ala Ile His Glu
121             125                 130                 135

Leu Ile Gln Val Met Ala Glu Leu Ser Pro Ala Ala Lys Thr Gly
136             140                 145                 150

Lys Arg Lys Arg Ser Gln Met Leu Phe Arg Gly Arg Arg Ala Ser
151             155                 160                 165

Gln
166
```

Polyclonal antibodies to gamma interferon may be obtained using the whole molecule of gamma interferon of the following sequence:

SEQ. ID. NO. 2

```
Met Lys Tyr Thr Ser Tyr Ile Leu Ala Phe Gln Leu Cys Ile Val
1               5                   10                  15

Leu Gly Ser Leu Gly Cys Tyr Cys Gln Asp Pro Tyr Val Lys Glu
16              20                  25                  30

Ala Glu Asn Leu Lys Lys Tyr Phe Asn Ala Gly His Ser Asp Val
31              35                  40                  45

Ala Asp Asn Gly Thr Leu Phe Leu Gly Ile Leu Lys Asn Trp Lys
46              50                  55                  60

Glu Glu Ser Asp Arg Lys Ile Met Gln Ser Gln Ile Val Ser Phe
61              65                  70                  75

Tyr Phe Lys Leu Phe Lys Asn Phe Lys Asp Asp Gln Ser Ile Gln
76              80                  85                  90

Lys Ser Val Glu Thr Ile Lys Glu Asp Met Asn Val Lys Phe Phe
91              95                  100                 105

Asn Ser Asn Lys Lys Lys Arg Asp Asp Phe Glu Lys Leu Thr Asn
106             110                 115                 120

Tyr Ser Val Thr Asp Leu Asn Val Gln Arg Lys Ala Ile His Glu
121             125                 130                 135

Leu Ile Gln Val Met Ala Glu Leu Ser Pro Ala Ala Lys Thr Gly
136             140                 145                 150

Lys Arg Lys Arg Ser Gln Met Leu Phe Gln Gly Arg Arg Ala Ser
151             155                 160                 165

Gln
166
```

The use of gamma interferon fragments as antigen is also contemplated. The suitable sequence for such antigen is as follow:

SEQ. ID. NO 3

```
              Ile Leu Ala Phe Gln Leu Cys Ile Val
               7          10              15
Leu Gly Ser Leu Gly Cys Tyr Cys Gln Asp Pro Tyr Val Lys Glu
16          20              25              30
Ala Glu Asn Leu Lys Lys Tyr Phe Asn Ala Gly His Ser Asp Val
31          35              40              45
Ala Asp Asn Gly Thr Leu Phe Leu Gly Ile
46          50              55
```

SEQ. ID. NO 4

```
                          Gln Asp Pro Tyr Val Lys Glu
                           24              30
Ala Glu Asn Leu Lys Lys Tyr Phe Asn Ala Gly His Ser Asp Val
31          35              40              45
Ala Asp Asn Gly Thr Leu Phe Leu Gly Ile Leu Lys Asn Trp Lys
46          50              55              60
Glu Glu Ser Asp Arg Lys Ile Met Gln Ser Gln Ile Val Ser Phe
61          65              70              75
Tyr Phe Lys Leu Phe Lys Asn Phe Lys Asp Asp Gln Ser Ile Gln
76          80              85              90
Lys Ser Val Glu Thr Ile Lys Glu Asp Met Asn Val Lys Phe Phe
91          95              100             105
Asn Ser Asn Lys Lys Lys Arg Asp Asp Phe Glu Lys Leu Thr Asn
106         110             115             120
Tyr Ser Val Thr Asp Leu Asn Val Gln Arg Lys Ala Ile His Glu
121         125             130             135
Leu Ile Gln Val Met Ala Glu Leu Ser Pro Ala Ala Lys Thr Gly
136         140             145             150
Lys Arg Lys Arg Ser Gln Met Leu Phe Arg Gly Arg Arg Ala Ser
151         155             160             165
Gln
166
```

SEQ. ID. NO 5

```
                          Gln Asp Pro Tyr Val Lys Glu
                           24              30
Ala Glu Asn Leu Lys Lys Tyr Phe Asn Ala Gly His Ser Asp Val
31          35              40              45
Ala Asp Asn Gly Thr Leu Phe Leu Gly Ile Leu Lys Asn Trp Lys
46          50              55              60
Glu Glu Ser Asp Arg Lys Ile Met Gln Ser Gln Ile Val Ser Phe
61          65              70              75
Tyr Phe Lys Leu Phe Lys Asn Phe Lys Asp Asp Gln Ser Ile Gln
76          80              85              90
Lys Ser Val Glu Thr Ile Lys Glu Asp Met Asn Val Lys Phe Phe
91          95              100             105
Asn Ser Asn Lys Lys Lys Arg Asp Asp Phe Glu Lys Leu Thr Asn
106         110             115             120
Tyr Ser Val Thr Asp Leu Asn Val Gln Arg Lys Ala Ile His Glu
121         125             130             135
Leu Ile Gln Val Met Ala Glu Leu Ser Pro Ala Ala Lys Thr Gly
136         140             145             150
```

-continued

```
Lys Arg Lys Arg Ser Gln Met Leu Phe Gln Gly Arg Ala Ser
151             155                 160                 165

Gln
166
```

```
                                                      SEQ. ID. NO 6
                        Gln Ser Gln Ile Val Ser Phe
                         69                      75

Tyr Phe Lys Leu Phe Lys Asn Phe Lys Asp Asp Gln Ser Ile Gln
 76             80                  85                  90

Lys Ser Val Glu Thr Ile Lys Glu Asp Met Asn Val Lys Phe Phe
 91             95                 100                 105

Asn Ser Asn Lys Lys Lys Arg Asp Asp Phe Glu Lys Leu Thr Asn
106             110                 115                 120

Tyr Ser Val
121     123
```

```
                                                      SEQ. ID. NO 7
                        Met Asn Val Lys Phe Phe
                        100                 105

Asn Ser Asn Lys Lys Lys Arg Asp Asp Phe Glu Lys Leu Thr Asn
106             110                 115                 120

Tyr Ser Val Thr Asp Leu Asn Val Gln Arg Lys Ala Ile His Glu
121             125                 130                 135

Leu Ile Gln Val Met Ala Glu Leu Ser Pro
136             140                 145
```

```
                                                      SEQ. ID. NO 8
    Ser Val Glu Thr Ile Lys Glu Asp Met Asn Val Lys Phe Phe
     92             95                 100                 105

Asn Ser Asn Lys Lys Lys Arg Asp Asp Phe Glu Lys Leu Thr Asn
106             110                 115                 120

Tyr Ser Val Thr Asp Leu Asn Val Gln Arg
121             125                 130
```

```
                                                      SEQ. ID. NO 9
    Val Thr Asp Leu Asn Val Gln Arg Lys Ala Ile His Glu
        123     125                 130                 135

Leu Ile Gln Val Met Ala Glu Leu Ser Pro Ala Ala
136             140                 145     147
```

```
                                                      SEQ. ID. NO 10
            Ser Tyr Ile Leu Ala Phe Gln Leu Cys Ile Val
                 5                  10
 15
Leu Gly Ser Leu Gly Cys Tyr Cys Gln Asp Pro Tyr Val Lys Glu
 16             20                  25                  30

Ala Glu Asn Leu Lys Lys Tyr Phe Asn Ala Gly His Ser Asp Val
 31             35                  40                  45
```

```
                                                      SEQ. ID. NO 11
            Glu Thr Ile Lys Glu Asp Met Asn Val Lys Phe Phe
                 94                 100
105
Asn Ser Asn Lys Lys Lys Arg Asp Asp
106             110                 115
```

Polyclonal antibodies to gamma interferon may be obtained using the molecule of recombinant gamma interferon of one of the following sequences:

SEQ. ID. NO 12

```
            Met Gln Asp Pro Tyr Val Lys Glu
                 24                      30
Ala Glu Asn Leu Lys Lys Tyr Phe Asn Ala Gly His Ser Asp Val
 31             35                  40                  45
Ala Asp Asn Gly Thr Leu Phe Leu Gly Ile Leu Lys Asn Trp Lys
 46             50                  55                  60
Glu Glu Ser Asp Arg Lys Ile Met Gln Ser Gln Ile Val Ser Phe
 61             65                  70                  75
Tyr Phe Lys Leu Phe Lys Asn Phe Lys Asp Asp Gln Ser Ile Gln
 76             80                  85                  90
Lys Ser Val Glu Thr Ile Lys Glu Asp Met Asn Val Lys Phe Phe
 91             95                 100                 105
Asn Ser Asn Lys Lys Lys Arg Asp Asp Phe Glu Lys Leu Thr Asn
106            110                 115                 120
Tyr Ser Val Thr Asp Leu Asn Val Gln Arg Lys Ala Ile His Glu
121            125                 130                 135
Leu Ile Gln Val Met Ala Glu Leu Ser Pro Ala Ala Lys Thr Gly
136            140                 145                 150
Lys Arg Lys Arg Ser Gln Met Leu Phe Gln Gly Arg Arg Ala Ser
151            155                 160                 165
Gln
166
```

SEQ. ID. NO 13

```
            Met Gln Asp Pro Tyr Val Lys Glu
                 24                      30
Ala Glu Asn Leu Lys Lys Tyr Phe Asn Ala Gly His Ser Asp Val
 31             35                  40                  45
Ala Asp Asn Gly Thr Leu Phe Leu Gly Ile Leu Lys Asn Trp Lys
 46             50                  55                  60
Glu Glu Ser Asp Arg Lys Ile Met Gln Ser Gln Ile Val Ser Phe
 61             65                  70                  75
Tyr Phe Lys Leu Phe Lys Asn Phe Lys Asp Asp Gln Ser Ile Gln
 76             80                  85                  90
Lys Ser Val Glu Thr Ile Lys Glu Asp Met Asn Val Lys Phe Phe
 91             95                 100                 105
Asn Ser Asn Lys Lys Lys Arg Asp Asp Phe Glu Lys Leu Thr Asn
106            110                 115                 120
Tyr Ser Val Thr Asp Leu Asn Val Gln Arg Lys Ala Ile His Glu
121            125                 130                 135
Leu Ile Gln Val Met Ala Glu Leu Ser Pro Ala Ala Lys Thr Gly
136            140                 145                 150
Lys Arg Lys Arg Ser Gln Met Leu Phe Arg Gly Arg Arg Ala Ser
151            155                 160                 165
Gln
166
```

The exemplary procedure for preparation of the starting polyclonal antibodies to human gamma interferon may be described as follows. In 7-9 days before blood sampling, 1-3 intravenous injections of the desired antigen are made to the rabbits to increase the level of polyclonal antibodies in the rabbit blood stream. Upon immunization, blood samples are taken to test the antibody level. Typically, the maximum level of immune reaction of the soluble antigen is achieved within 40 to 60 days after the first injection of the antigen. Upon completion of the first immunization cycle, rabbits have a 30-day rehabilitation period, after which re-immunization is performed with another 1-3 intravenous injections.

To obtain antiserum containing the desired antibodies, the immunized rabbits' blood is collected from rabbits and placed in a 50 ml centrifuge tube. Product clots formed on the tube sides are removed with a wooden spatula, and a rod is placed into the clot in the tube center. The blood is then placed in a refrigerator for one night at the temperature of about 40° C. On the following day, the clot on the spatula is removed, and the remaining liquid is centrifuged for 10 min at 13,000 rotations per minute. Supernatant fluid is the target antiserum. The obtained antiserum is typically yellow. 20% of $NaN_3$ (weight concentration) is added in the antiserum to a final concentration of 0.02% and stored before use in frozen state at the temperature of −20° C. or without $NaN_3$ at the temperature of −70° C. To separate the target antibodies to gamma interferon from the antiserum, the following solid phase absorption sequence is suitable:

10 ml of the antiserum of rabbits is diluted twofold with 0.15 M NaCl, after which 6.26 g $Na_2SO_4$ is added, mixed and incubated for 12-16 hours at 4° C. The sediment is removed by centrifugation, diluted in 10 ml of phosphate buffer and dialyzed against the same buffer during one night at ambient temperature. After the sediment is removed, the solution is applied to a DEAE-cellulose column balanced by phosphate buffer. The antibody fraction is determined by measuring the optical density of the eluate at 280 nm.

The isolated crude antibodies are purified using affine chromatography method by attaching the obtained antibodies to gamma interferon located in the insoluble matrix of the chromatography media, with subsequent elution by concentrated aqueous salt solutions.

The resulting buffer solution is used as the initial solution for the homeopathic dilution process used to prepare the activated potentiated form of the antibodies. The preferred concentration of the initial matrix solution of the antigen-purified polyclonal rabbit antibodies to gamma interferon is 0.5 to 5.0 mg/ml, preferably, 2.0 to 3.0 mg/ml.

The brain-specific S100 protein, expressed by neurons and glial cells (astrocytes and oligodendrocytes), directly or through interactions with other proteins executes in the CNS a number of functions directed at maintaining normal brain functioning, including affecting learning and memory processes, growth and viability of neurons, regulation of metabolic processes in neuronal tissues and others. To prepare the activated-potentiated form of antibodies, an antiserum to brain-specific S-100 protein may be removed from the brain tissue of a bull and processed as follows:

the bull brain tissue frozen in liquid nitrogen is converted into powder using a specialized mill;

proteins are extracted in the ratio of 1:3 (weight/volume) using an extracting buffer with homogenization;

the homogenate is heated for 10 min at 60° C. and then cooled to 4° C. in an ice bath;

thermolabile proteins are removed by centrifugation;

ammonium sulfate fractionation is carried out in stages, with subsequent removal of precipitated proteins;

the fraction containing S-100 protein is precipitated using 100% saturated ammonium sulfate accomplished by pH drop to 4.0; the desired fraction is collected by centrifugation;

the precipitate is dissolved in a minimum buffer volume containing EDTA and mercaptoethanol, the precipitate is dialyzed with deionized water and lyophilized;

fractionation of acidic proteins is followed by chromatography in ion-exchanging media, DEAE-cellulose DE-52 and then DEAE-sephadex A-50;

the collected and dialyzed fractions, which contain S-100 protein, are divided according to molecular weight by gel filtration on sephadex G-100;

purified S-100 protein is dialyzed and lyophilized.

The molecular weight of the purified brain-specific S-100 protein is 21000 D.

The polyclonal antibodies to S-100 protein may also be obtained by a similar methodology to the methodology described for gamma interferon antibodies using an adjuvant. The entire molecule of S-100 protein may be used as immunogen (antigen) for rabbits' immunization.

```
Bovine S100B
                                                      (SEQ. ID. NO. 14)
Met Ser Glu Leu Glu Lys Ala Val Val Ala Leu Ile Asp Val Phe
1               5                   10                  15

His Gln Tyr Ser Gly Arg Glu Gly Asp Lys His Lys Leu Lys Lys
16              20                  25                  30

Ser Glu Leu Lys Glu Leu Ile Asn Asn Glu Leu Ser His Phe Leu
31              35                  40                  45

Glu Glu Ile Lys Glu Gln Glu Val Val Asp Lys Val Met Glu Thr
46              50                  55                  60

Leu Asp Ser Asp Gly Asp Gly Glu Cys Asp Phe Gln Glu Phe Met
61              65                  70                  75

Ala Phe Val Ala Met Ile Thr Thr Ala Cys His Glu Phe Phe Glu
76              80                  85                  90

His Glu
91  92

Human S100B
                                                      (SEQ. ID. 15)
Met Ser Glu Leu Glu Lys Ala Met Val Ala Leu Ile Asp Val Phe
1               5                   10                  15

His Gln Tyr Ser Gly Arg Glu Gly Asp Lys His Lys Leu Lys Lys
16              20                  25                  30

Ser Glu Leu Lys Glu Leu Ile Asn Asn Glu Leu Ser His Phe Leu
31              35                  40                  45
```

-continued

```
Glu Glu Ile Lys Glu Gln Glu Val Val Asp Lys Val Met Glu Thr
46              50              55                  60

Leu Asp Asn Asp Gly Asp Gly Glu Cys Asp Phe Gln Glu Phe Met
61              65              70                  75

Ala Phe Val Ala Met Val Thr Thr Ala Cys His Glu Phe Phe Glu
76              80              85                  90

His Glu
91  92
```

Human S100A1

(SEQ. ID. No. 16)

```
Met Gly Ser Glu Leu Glu Thr Ala Met Glu Thr Leu Ile Asn Val
1               5               10                  15

Phe His Ala His Ser Gly Lys Glu Gly Asp Lys Tyr Lys Leu Ser
16              20              25                  30

Lys Lys Glu Leu Lys Glu Leu Leu Gln Thr Glu Leu Ser Gly Phe
31              35              40                  45

Leu Asp Ala Gln Lys Asp Val Asp Ala Val Asp Lys Val Met Lys
46              50              55                  60

Glu Leu Asp Glu Asn Gly Asp Gly Glu Val Asp Phe Gln Glu Tyr
61              65              70                  75

Val Val Leu Val Ala Ala Leu Thr Val Ala Cys Asn Asn Phe Phe
76              80              85                  90

Trp Glu Asn Ser
91          94
```

Bovine S100A1

(SEQ. ID. NO. 17)

```
Met Gly Ser Glu Leu Glu Thr Ala Met Glu Thr Leu Ile Asn Val
1               5               10                  15

Phe His Ala His Ser Gly Lys Glu Gly Asp Lys Tyr Lys Leu Ser
16              20              25                  30

Lys Lys Glu Leu Lys Glu Leu Leu Gln Thr Glu Leu Ser Gly Phe
31              35              40                  45

Leu Asp Ala Gln Lys Asp Ala Asp Ala Val Asp Lys Val Met Lys
46              50              55                  60

Glu Leu Asp Glu Asn Gly Asp Gly Glu Val Asp Phe Gln Glu Tyr
61              65              70                  75

Val Val Leu Val Ala Ala Leu Thr Val Ala Cys Asn Asn Phe Phe
76              80              85                  90

Trp Glu Asn Ser
91          94
```

To obtain brain-specific antiserum to separated brain-specific S-100 protein, a mixture of purified S-100 protein (antigen) may be prepared in complex by methylated bull serum albumin as the medium with complete Freund's adjuvant, which is subcutaneously injected in the laboratory animal, rabbit, in the area of the spine in the quantity of 1-2 ml. The antiserum may have a titer of 1:500-1:1000.

The activated potentiated form of each component of the combination may be prepared from an initial solution by homeopathic potentization, preferably using the method of proportional concentration decrease by serial dilution of 1 part of each preceding solution (beginning with the initial solution) in 9 parts (for decimal dilution), or in 99 parts (for centesimal dilution), or in 999 parts (for millesimal dilution) of a neutral solvent, starting with a concentration of the initial solution of antibody in the solvent, preferably, water or a water-ethyl alcohol mixture, in the range from about 0.5 to about 5.0 mg/ml, coupled with external impact. Preferably, the external impact involves multiple vertical shaking (dynamization) of each dilution. Preferably, separate containers are used for each subsequent dilution up to the required potency level, or the dilution factor. This method is well-accepted in the homeopathic art. See, e.g. V. Schwabe "*Homeopathic medicines*", M., 1967, p. 14-29, incorporated herein by reference for the purpose stated.

For example, to prepare a 12-centesimal dilution (denoted C12), one part of the initial matrix solution of antibodies to gamma interferon with the concentration of 3.0 mg/ml is diluted in 99 parts of neutral aqueous or aqueous-alcohol solvent (preferably, 15%-ethyl alcohol) and then vertically shaked many times (10 and more) to create the 1st centesimal dilution (denoted as C1). The 2nd centesimal dilution (C2) is prepared from the 1st centesimal dilution C1. This procedure is repeated 11 times to prepare the 12th centesimal dilution C12. Thus, the 12th centesimal dilution C12 represents a solution obtained by 12 serial dilutions of one part of the initial matrix solution of antibodies to gamma interferon with the concentration of 3.0 mg/ml in 99 parts of a neutral solvent in different containers, which is equivalent to the centesimal homeopathic dilution C12. Similar procedures with the relevant dilution factor are performed to obtain dilutions C30, C50 and C200. The intermediate dilutions may be tested in a desired biological model to check activity. The preferred activated potentiated forms for both antibodies comprising the combination of the invention are a mixture of C12, C30, and C50 dilutions or C12, C30 and C200 dilutions. When using the mixture of various homeopathic dilutions (primarily centesimal) of the active substance as biologically active liquid component, each component of the composition (e.g., C12, C30, C50, C200) is prepared separately according to the above-described procedure until the next-to-last dilution is obtained (e.g., until C11, C29, and C199 respectively), and then one part of each component is added in one container according to the mixture composition and mixed with the required quantity of the solvent (e.g. with 97 parts for centesimal dilution).

It is possible to use the active substance as mixture of various homeopathic dilutions, e.g. decimal and/or centesimal (D20, C30, C100 or C12, C30, C50 or C12, C30, C200, etc.), the efficiency of which is determined experimentally by testing the dilution in a suitable biological model, for example, in models described in the examples herein.

In the course of potentiation and concentration decrease, the vertical shaking may be substituted for external exposure to ultrasound, electromagnetic field or any similar external impact procedure accepted in the homeopathic art.

Preferably, the pharmaceutical composition of the invention may be in the form of a liquid or in the solid unit dosage form. The preferred liquid form of the pharmaceutical composition is a mixture, preferably, at a 1:1 ratio of the activated potentiated form of antibodies to gamma interferon and the activated potentiated form of antibodies to S-100 protein. The preferred liquid carrier is water or water-ethyl alcohol mixture.

The solid unit dosage form of the pharmaceutical composition of the invention may be prepared by impregnating a solid, pharmaceutically acceptable carrier with the mixture of the activated potentiated form aqueous or aqueous-alcohol solutions of active components that are mixed, preferably in 1:1 ratio. Alternatively, the carrier may be impregnated consecutively with each requisite dilution. Both orders of impregnation are acceptable.

Preferably, the pharmaceutical composition in the solid unit dosage form is prepared from granules of the pharmaceutically acceptable carrier which was previously saturated with the aqueous or aqueous-alcoholic dilutions of the activated potentiated form of antibodies to gamma interferon and the activated potentiated form of antibodies to S-100 protein. The solid dosage form may be in any form known in the pharmaceutical art, including a tablet, a capsule, a lozenge, and others. As an inactive pharmaceutical ingredients one can use glucose, sucrose, maltose, amylum, isomaltose, isomalt and other mono-olygo- and polysaccharides used in manufacturing of pharmaceuticals as well as technological mixtures of the above mentioned inactive pharmaceutical ingredients with other pharmaceutically acceptable excipients, for example isomalt, crospovidone, sodium cyclamate, sodium saccharine, anhydrous citric acid etc), including lubricants, disintegrants, binders and coloring agents. The preferred carriers are lactose and isomalt. The pharmaceutical dosage form may further include standard pharmaceutical excipients, for example, microcrystalline cellulose and magnesium stearate.

To prepare the solid oral form, 100-300 μm granules of lactose are impregnated with aqueous or aqueous-alcoholic solutions of the activated potentiated form of antibodies to histamine, activated-potentiated form of antibodies to gamma-interferon and the activated potentiated form of antibodies to S-100 protein in the ratio of 1 kg of antibody solution to 5 or 10 kg of lactose (1:5 to 1:10). To effect impregnation, the lactose granules are exposed to saturation irrigation in the fluidized boiling bed in a boiling bed plant (e.g. "Hüttlin Pilotlab" by Hüttlin GmbH) with subsequent drying via heated air flow at a temperature below 40° C. The estimated quantity of the dried granules (10 to 34 weight parts) saturated with the activated potentiated form of antibodies is placed in the mixer, and mixed with 25 to 45 weight parts of "non-saturated" pure lactose (used for the purposes of cost reduction and simplification and acceleration of the technological process without decreasing the treatment efficiency), together with 0.1 to 1 weight parts of magnesium stearate, and 3 to 10 weight parts of microcrystalline cellulose. The obtained tablet mass is uniformly mixed, and tableted by direct dry pressing (e.g., in a Korsch-XL 400 tablet press) to form 150 to 500 mg round pills, preferably, 300 mg. After tableting, 300 mg pills are obtained that are saturated with aqueous-alcohol solution (3.0-6.0 mg/pill) of the combination of the activated potentiated form of antibodies to gamma interferon and the activated potentiated form of antibodies to S-100 protein. Each component of the combination used to impregnate the carrier is in the form of a mixture of centesimal homeopathic dilutions C12, C30, and C50 or a mixture of centesimal homeopathic dilutions C12, C30 and C200.

While the invention is not limited to any specific theory, it is believed that the activated potentiated form of the antibodies described herein do not contain the molecular form of the antibody in an amount sufficient to have biological activity attributed to such molecular form. The biological activity of the combination drug (combination pharmaceutical composition) of the invention is amply demonstrated in the appended examples.

The present invention further provides a method of significantly delaying the onset of symptoms of multiple sclerosis, said method comprising administering a combination pharmaceutical composition comprising a) an activated-potentiated form of an antibody to gamma interferon, and b) an activated-potentiated form of an antibody to S-100 protein.

The present invention further provides a method of reducing the probability of relapse of episodes in a patient suffering from multiple sclerosis by administration of a combination pharmaceutical composition comprising a) an activated-potentiated form of an antibody to gamma interferon, and b) an activated-potentiated form of an antibody to S-100 protein.

Preferably, for the purpose of treatment, the combination of the invention is administered from once daily to four times daily, preferably twice daily, each administration including one or two combination unit dosage forms.

The invention is further illustrated with reference to the appended non-limiting examples.

EXAMPLES

Example 1

In this study female rats of the Wistar line (200-220 g) were used. EAE was induced in them by single inoculation of encephalitogenic mixture based on 100 mH of homogenate of homologous spinal cord, 0.2 ml CFA (content of killed mycobacteria 5 mg/ml) and 0.2 ml of physiological solution to one animal. The EGS was administered subcutaneously (at the base of the tail along the tail vein) under light ether anesthesia in the amount of 0.4 ml (0.2 ml on the right and left) (Abdurasulova, I. N., et al, 2004; Zhitnukhin, Y. L., et al, 2008; Serebryanaya, N. B., et al, 2010). The following were administered intragastrically 2 times a day at 7-hour intervals over 30 days, beginning from the day of EAE induction: (a) Ultra low dose of antibodies to S-100 protein (hereinafter "ULD Abs to S-100 protein") (n=10, 2.5 ml/kg/day); (b) ultra low dose of antibodies to gamma interferon (hereinafter "ULD Abs to γ-IFN") (n=10, 2.5 ml/kg/day); (c) the combination of ULD Abs to S-100 protein and ULD Abs to γ-IFN (hereinafter "the complex combination") (n=10, 5 ml/kg/day) and (d) the distilled water (control; n=10, 5 ml/kg/day). As a reference preparation, the immunomodulator Copaxone® (Teva, Israel) was used, which was administered intramuscularly at the dose of 4 mg/kg, from the 2nd to the 25th day after EAE induction. The results are shown on FIG. 2-5.

Clinical symptoms of experimental autoimmune encephalomyelitis (EAE) were assessed daily for 30 days starting on the day of induction of experimental autoimmune encephalomyelitis (EAE). Examination of each rat was carried out immediately before administration of drugs under study. In case of rapid disease progression the clinical symptoms were assessed twice daily.

The severity of neurological abnormalities was assessed in points: presence of muscle weakness, tremor (0.5 point); resistant paresis (1 point); paralysis (1.5 points). Clinical Index (CI) was calculated as a sum of the symptoms for 4 limbs. In addition, CI was designated as zero if visible clinical signs of neurologic abnormalities were absent, and designated as 6 in case of animal death. The maximal CI value was taken into account at all days. Cumulative index for each rat calculated as a sum of individual CI over total disease period (30 days) was recorded. The 30-day disease period was divided into the following phases: latent phase (1-10 days); clinical manifestation phase (11-18 days); and recovery phase (19-30 days).

To assess the efficacy of drugs under study in the model of Experimental autoimmune encephalomyelitis (EAE), the following parameters were assessed in each study group: 1) time of disease onset (days); 2) changes of mean severity of the disease over time (CI, points); 3) mean severity of the disease at different phases (CI, points) 4) total number of relapses, return of disease symptoms (%).

ULD Abs to S-100 protein moved back the onset of manifestation of clinical symptoms of disease periods, both in comparison with the negative control ($p<0.05$) and in comparison with Copaxone ($p>0.05$). The onset of disease in two groups that received ULD Abs to γ-IFN and in a group that received Copaxone did not differ from the control. See FIG. 2. At the same time, in animals that were administered the complex combination, the tendency was observed to shortening of period of appearance of clinical signs of multiple sclerosis in comparison with the control. It should be noted that statistically significant differences were revealed in the time of disease onset period between the group receiving ULD Abs to S-100 protein and the group receiving the complex combination.

The proportion of animals with severe course of disease (>3 points) was also lower in the group receiving ULD Abs to S-100 protein. In the groups that received the complex combination the percentage of animals with severe course was higher than in the other groups studied in all disease periods. See FIG. 3.

In connection with the fact that, at various phases in the development of multiple sclerosis, different mechanisms of EAE pathogenesis were activated, the effect of the preparations on disease severity in the latent period, in the development of clinical signs phase and in the recovery phase was analyzed. Administration of ULD Abs to S-100 protein significantly contributed to reducing the average points of manifestation of clinical signs of disease in the clinical manifestation stage and in the recovery stage, while Copaxone and ULD Abs to γ-IFN significantly reduced the severity of the clinical symptoms only in the last phase. The complex combination, in comparison with the control and the groups receiving ULD Abs to γ-IFN alone or ULD Abs to S-100 protein alone, statistically significant increased the average points of the affection of animals in the appearance of clinical signs of disease stage and in the recovery stage. See FIG. 4.

It should be noted that in a portion of the animals, after complete disappearance of the clinical signs of disease, a certain similarity to relapse, was noted, that is, the return of clinical manifestations of EAE. In the ULD Abs to S-100 protein group, in spite of its beneficial effect on the clinical course of EAE (later period of disease onset, lesser severity of manifestation of clinical signs), the greatest number of animals (25%) with relapses is noted. At the same time, in the complex combination group, which was characterized by early onset of disease and greater manifestation of pathologic process, no animal showed the development of relapses. See FIG. 5.

Conclusions:

In the model of experimental autoimmune encephalomyelitis (EAE), ULD Abs to S-100 protein had a beneficial effect on the course of the disease. ULD Abs to S-100 protein diminished the clinical signs of the disease during an episode and reduced severity of symptoms. ULD Abs to γ-IFN and Copaxone comparison preparation did not have an effect on the course of decease in the chosen experimental model of multiple sclerosis, that is for these substances, the magnitude of clinical signs of disease periods and the severity of symptoms did not differ from the control (distilled water).

Manifestation of the effects of preparations depended on the stage of development of EAE (latent phase, clinical signs phase, recovery phase).

The effect of the complex combination differed from the effect of the components, namely, from ULD Abs to S-100 protein or ULD Abs to γ-IFN alone. Use of the complex combination led to strengthening of the immune response. The complex combination led to earlier onset of disease, increase in the portion of sick animals and severity of disease.

25% of animals in the ULD Abs to S-100 protein group and 15% of animals in the ULD Abs to γ-IFN group showed relapse during the study period (30 days). At the same time, relapse was not recorded in any animal in the complex combination group.

The most common course of multiple sclerosis is the relapsing-remitting subtype, which is characterized by unpredictable attacks (relapses), followed by periods of relative remission with no new signs of disease activity.

The primary aims of multiple sclerosis therapy are reducing the neuronal damage during an acute attack and returning function after an attack, as well as preventing new attacks leading to disability.

ULD Abs to S100 protein alone was able to ameliorate clinical symptoms of EAE during all phases of experimental disease that makes it potentially useful in the treatment of multiple sclerosis attacks. The combination of ULD Abs to S100 protein+ULD Abs to γ-IFN completely prevented return of clinical symptoms of EAE, and thus, can be used in the treatment of multiples sclerosis in humans as a means of prevention of relapse. Thus, the combination of ULD Abs to S-100 protein+ULD Abs to γ-IFN is a promising preparation for treating multiple sclerosis, which, it is believed, by strengthening of immune response at the peak of disease development, can contribute to more effective rehabilitation and prevention of relapses.

Example 2

Sigma-1 receptor—an intracellular receptor localized in the cells of central nervous system, the cells of the most of peripheral tissues, and immune cells. It is believed that this receptor, through control of homeostasis of intracellular calcium, regulates intracellular signaling events leading to activation of the corresponding transcription factors and transcription of a whole gene family. Sigma-1 receptor is involved in the pathogenesis of various diseases including, lemic and neurodegenerative conditions. In this regard, drugs influencing this receptor and the efficiency of interaction of ligands with this receptor may be regarded as effective drugs for the treatment of neuroinfectious and neurodegenerative diseases.

protein and ULD Abs to γ-IFN introduced into the experimental well during testing of the complex combination was identical to the quantity of ULD Abs to S100 protein and ULD Abs to γ-IFN tested as monopreparations, thus making it possible to compare the effectiveness of the complex combination with the separate components that constitute the complex composition. Potentiated water was introduced in the incubation medium in the amount of 20 μl and 10 μl.

Then 160 μl (~200 μg of protein) of homogenate of Jurkat line cell membranes (line of human leukemic T-lymphocytes) was introduced, followed by 20 μl of the tritium-labeled radioligand [$^3$H]pentazocine (15 nM).

For measuring nonspecific bonding, instead of the preparations or potentiated water, 20 μl of the unlabeled ligand Haloperidol (10 μM) was introduced in the incubation medium.

Radioactivity was measured on a scintillation counter (Topcount, Packard) with use of a scintillation mixture (Microscint 0, Packard) after incubation for 120 minutes at 22° C. in 50 mM Tris-HCL buffer (pH=7.4) and filtration on fiberglass filters (GF/B, Packard). Specific binding (in the experiment or control) was calculated as the difference between covalent (in experiment or control) and nonspecific bonding.

Results (in measurement of covalent binding) are represented as a percentage of specific binding inhibition in the control (potentiated water was used as the control) (see Table 4).

TABLE 4

Effect of test preparations and potentiated water on binding of standard radioligand [$^3$H]pentazocine with recombinant human sigma 1 receptor

| Experimental group | Quantity introduced in experimental well | % of specific binding of radioligand in control | | | % of inhibition of radioligand binding in control |
|---|---|---|---|---|---|
| | | 1st measurement | 2nd measurement | Average value | |
| Complex Combination | 20 μl | 44.2 | 46.2 | 45.2 | 54.8 |
| ULD Abs to S-100 protein | 10 μl | 70.9 | 62.9 | 66.9 | 33.1 |
| ULD Abs to γ-IFN | 10 μl | 158.9 | 149.8 | 154.3 | −54.3 |
| Potentiated water | 20 μl | 98.1 | 75.8 | 86.9 | 13.1 |
| Potentiated water | 10 μl | 140.1 | 106.2 | 123.2 | −23.2 |

% of specific bonding in control = (specific bonding in experiment/specific bonding in control) * 100%;
% of specific bonding inhibition in control = 100% − (specific bonding in experiment/specific bonding in control) * 100%).

The effect of the complex combination whose composition includes ultra-low doses of S100 protein antibodies (mixture of homeopathic dilutions C12+C30+C50) and ultra-low doses of interferon gamma antibodies (mixture of homeopathic dilutions C12+C30+C50) in the ratio 1:1, and also components of the composition (ultra-low doses of S100 protein antibodies (mixture of homeopathic dilutions C12+C30+C50) (ULD Abs to S-100 protein) and ultra-low doses of interferon gamma antibodies (mixture of homeopathic dilutions C12+C30+C50) (ULD Abs to γ-IFN)), were investigated in vitro on binding of standard ligand [$^3$H]pentazocine with recombinant human sigma 1 receptor and evaluated by radioligand method. As control, potentiated distilled water (mixture of homeopathic dilutions C12+C30+C50) (potentiated water) was tested.

20 μl of the complex combination or 10 μl of ULD Abs to S100 protein or ULD Abs to γ-IFN was introduced in the incubation medium. Thus, the quantity of ULD Abs to S100

Inhibition of over 50% shows that there exists a significant effect on binding. Inhibition from 25% to 50% shows weak to moderate effects. Inhibition of less than 25% are considered insignificant in terms of effect on binding, and are within background limits.

Conclusion:

The complex combination more effectively inhibits binding of standard radioligand [$^3$H]pentazocine with recombinant human sigma 1 receptor than its separate components (ULD Abs to S100 protein or ULD Abs to γ-IFN).

ULD Abs to S100 protein, introduced in an experimental well in the amount of 10 μl, inhibits the binding of standard radioligand [$^3$H]pentazocine with recombinant human sigma 1 receptor, but expression of the effect is inferior to expression of the effect with the complex combination.

ULD Abs to γ-IFN, introduced in an experimental well in the amount of 10 μl, did not have an effect on the binding of standard radioligand [$^3$H]pentazocine with recombinant human sigma 1 receptor.

Potentiated water, introduced in an experimental well in the amount of 10 μl or 20 μl, did not have an effect on the binding of standard radioligand [³H]pentazocine with recombinant human sigma 1 receptor.

What is claimed is:

1. A method of treating multiple sclerosis, said method comprising administering to a patient in need thereof, substantially at the same time, a) a therapeutically effective amount of an activated-potentiated form of an antibody to gamma interferon, and b) a therapeutically effective amount of an activated-potentiated form of an antibody to S-100 protein.

2. The method of claim 1, wherein said activated-potentiated form of an antibody to gamma interferon and said activated-potentiated form of an antibody to S-100 protein are administered in the form of a combined pharmaceutical composition.

3. A method of reducing the frequency of appearance of relapse in a patient suffering from multiple sclerosis by administration of a therapeutically effective amount of the combined pharmaceutical composition of claim 2.

4. The method of claim 2, wherein the combined pharmaceutical composition is administered in one to two unit dosage forms, each of the dosage form being administered from once daily to four times daily.

5. The method of claim 2, wherein the combined pharmaceutical composition is administered in one to two unit dosage forms, each of the dosage form being administered twice daily.

* * * * *

```
                         SEQUENCE LISTING

<160> NUMBER OF SEQ ID NOS: 17

<210> SEQ ID NO 1
<211> LENGTH: 166
<212> TYPE: PRT
<213> ORGANISM: Homo sapiens
<220> FEATURE:
<221> NAME/KEY: SOURCE
<222> LOCATION: 1..166
<223> OTHER INFORMATION: /mol_type="protein"
      /organism="Homo sapiens"

<400> SEQUENCE: 1

Met Lys Tyr Thr Ser Tyr Ile Leu Ala Phe Gln Leu Cys Ile Val Leu
1               5                   10                  15

Gly Ser Leu Gly Cys Tyr Cys Gln Asp Pro Tyr Val Lys Glu Ala Glu
            20                  25                  30

Asn Leu Lys Lys Tyr Phe Asn Ala Gly His Ser Asp Val Ala Asp Asn
        35                  40                  45

Gly Thr Leu Phe Leu Gly Ile Leu Lys Asn Trp Lys Glu Glu Ser Asp
    50                  55                  60

Arg Lys Ile Met Gln Ser Gln Ile Val Ser Phe Tyr Phe Lys Leu Phe
65                  70                  75                  80

Lys Asn Phe Lys Asp Asp Gln Ser Ile Gln Lys Ser Val Glu Thr Ile
                85                  90                  95

Lys Glu Asp Met Asn Val Lys Phe Phe Asn Ser Asn Lys Lys Lys Arg
            100                 105                 110

Asp Asp Phe Glu Lys Leu Thr Asn Tyr Ser Val Thr Asp Leu Asn Val
        115                 120                 125

Gln Arg Lys Ala Ile His Glu Leu Ile Gln Val Met Ala Glu Leu Ser
    130                 135                 140

Pro Ala Ala Lys Thr Gly Lys Arg Lys Arg Ser Gln Met Leu Phe Arg
145                 150                 155                 160

Gly Arg Arg Ala Ser Gln
                165

<210> SEQ ID NO 2
<211> LENGTH: 166
<212> TYPE: PRT
<213> ORGANISM: Homo sapiens
<220> FEATURE:
<221> NAME/KEY: SOURCE
<222> LOCATION: 1..166
<223> OTHER INFORMATION: /mol_type="protein"
      /organism="Homo sapiens"

<400> SEQUENCE: 2

Met Lys Tyr Thr Ser Tyr Ile Leu Ala Phe Gln Leu Cys Ile Val Leu
1               5                   10                  15

Gly Ser Leu Gly Cys Tyr Cys Gln Asp Pro Tyr Val Lys Glu Ala Glu
            20                  25                  30

Asn Leu Lys Lys Tyr Phe Asn Ala Gly His Ser Asp Val Ala Asp Asn
        35                  40                  45

Gly Thr Leu Phe Leu Gly Ile Leu Lys Asn Trp Lys Glu Glu Ser Asp
    50                  55                  60

Arg Lys Ile Met Gln Ser Gln Ile Val Ser Phe Tyr Phe Lys Leu Phe
65                  70                  75                  80
```

```
Lys Asn Phe Lys Asp Asp Gln Ser Ile Gln Lys Ser Val Glu Thr Ile
                85                  90                  95

Lys Glu Asp Met Asn Val Lys Phe Phe Asn Ser Asn Lys Lys Lys Arg
            100                 105                 110

Asp Asp Phe Glu Lys Leu Thr Asn Tyr Ser Val Thr Asp Leu Asn Val
        115                 120                 125

Gln Arg Lys Ala Ile His Glu Leu Ile Gln Val Met Ala Glu Leu Ser
    130                 135                 140

Pro Ala Ala Lys Thr Gly Lys Arg Lys Arg Ser Gln Met Leu Phe Gln
145                 150                 155                 160

Gly Arg Arg Ala Ser Gln
                165

<210> SEQ ID NO 3
<211> LENGTH: 49
<212> TYPE: PRT
<213> ORGANISM: Homo sapiens
<220> FEATURE:
<221> NAME/KEY: SOURCE
<222> LOCATION: 1..49
<223> OTHER INFORMATION: /mol_type="protein"
      /organism="Homo sapiens"

<400> SEQUENCE: 3

Ile Leu Ala Phe Gln Leu Cys Ile Val Leu Gly Ser Leu Gly Cys Tyr
1               5                   10                  15

Cys Gln Asp Pro Tyr Val Lys Glu Ala Glu Asn Leu Lys Lys Tyr Phe
            20                  25                  30

Asn Ala Gly His Ser Asp Val Ala Asp Asn Gly Thr Leu Phe Leu Gly
        35                  40                  45

Ile

<210> SEQ ID NO 4
<211> LENGTH: 143
<212> TYPE: PRT
<213> ORGANISM: Homo sapiens
<220> FEATURE:
<221> NAME/KEY: SOURCE
<222> LOCATION: 1..143
<223> OTHER INFORMATION: /mol_type="protein"
      /organism="Homo sapiens"

<400> SEQUENCE: 4

Gln Asp Pro Tyr Val Lys Glu Ala Glu Asn Leu Lys Lys Tyr Phe Asn
1               5                   10                  15

Ala Gly His Ser Asp Val Ala Asp Asn Gly Thr Leu Phe Leu Gly Ile
            20                  25                  30

Leu Lys Asn Trp Lys Glu Glu Ser Asp Arg Lys Ile Met Gln Ser Gln
        35                  40                  45

Ile Val Ser Phe Tyr Phe Lys Leu Phe Lys Asn Phe Lys Asp Asp Gln
    50                  55                  60

Ser Ile Gln Lys Ser Val Glu Thr Ile Lys Glu Asp Met Asn Val Lys
65                  70                  75                  80

Phe Phe Asn Ser Asn Lys Lys Lys Arg Asp Asp Phe Glu Lys Leu Thr
                85                  90                  95

Asn Tyr Ser Val Thr Asp Leu Asn Val Gln Arg Lys Ala Ile His Glu
            100                 105                 110
```

-continued

Leu Ile Gln Val Met Ala Glu Leu Ser Pro Ala Ala Lys Thr Gly Lys
            115                 120                 125

Arg Lys Arg Ser Gln Met Leu Phe Arg Gly Arg Ala Ser Gln
    130                 135                 140

<210> SEQ ID NO 5
<211> LENGTH: 143
<212> TYPE: PRT
<213> ORGANISM: Homo sapiens
<220> FEATURE:
<221> NAME/KEY: SOURCE
<222> LOCATION: 1..143
<223> OTHER INFORMATION: /mol_type="protein"
      /organism="Homo sapiens"

<400> SEQUENCE: 5

Gln Asp Pro Tyr Val Lys Glu Ala Glu Asn Leu Lys Lys Tyr Phe Asn
1               5                   10                  15

Ala Gly His Ser Asp Val Ala Asp Asn Gly Thr Leu Phe Leu Gly Ile
            20                  25                  30

Leu Lys Asn Trp Lys Glu Glu Ser Asp Arg Lys Ile Met Gln Ser Gln
        35                  40                  45

Ile Val Ser Phe Tyr Phe Lys Leu Phe Lys Asn Phe Lys Asp Asp Gln
50                  55                  60

Ser Ile Gln Lys Ser Val Glu Thr Ile Lys Glu Asp Met Asn Val Lys
65                  70                  75                  80

Phe Phe Asn Ser Asn Lys Lys Arg Asp Asp Phe Glu Lys Leu Thr
                85                  90                  95

Asn Tyr Ser Val Thr Asp Leu Asn Val Gln Arg Lys Ala Ile His Glu
                100                 105                 110

Leu Ile Gln Val Met Ala Glu Leu Ser Pro Ala Ala Lys Thr Gly Lys
            115                 120                 125

Arg Lys Arg Ser Gln Met Leu Phe Gln Gly Arg Arg Ala Ser Gln
    130                 135                 140

<210> SEQ ID NO 6
<211> LENGTH: 55
<212> TYPE: PRT
<213> ORGANISM: Homo sapiens
<220> FEATURE:
<221> NAME/KEY: SOURCE
<222> LOCATION: 1..55
<223> OTHER INFORMATION: /mol_type="protein"
      /organism="Homo sapiens"

<400> SEQUENCE: 6

Gln Ser Gln Ile Val Ser Phe Tyr Phe Lys Leu Phe Lys Asn Phe Lys
1               5                   10                  15

Asp Asp Gln Ser Ile Gln Lys Ser Val Glu Thr Ile Lys Glu Asp Met
            20                  25                  30

Asn Val Lys Phe Phe Asn Ser Asn Lys Lys Arg Asp Asp Phe Glu
        35                  40                  45

Lys Leu Thr Asn Tyr Ser Val
    50                  55

<210> SEQ ID NO 7
<211> LENGTH: 46
<212> TYPE: PRT
<213> ORGANISM: Homo sapiens

```
<220> FEATURE:
<221> NAME/KEY: SOURCE
<222> LOCATION: 1..46
<223> OTHER INFORMATION: /mol_type="protein"
      /organism="Homo sapiens"

<400> SEQUENCE: 7

Met Asn Val Lys Phe Phe Asn Ser Asn Lys Lys Arg Asp Asp Phe
1               5                   10                  15

Glu Lys Leu Thr Asn Tyr Ser Val Thr Asp Leu Asn Val Gln Arg Lys
            20                  25                  30

Ala Ile His Glu Leu Ile Gln Val Met Ala Glu Leu Ser Pro
        35                  40                  45

<210> SEQ ID NO 8
<211> LENGTH: 39
<212> TYPE: PRT
<213> ORGANISM: Homo sapiens
<220> FEATURE:
<221> NAME/KEY: SOURCE
<222> LOCATION: 1..39
<223> OTHER INFORMATION: /mol_type="protein"
      /organism="Homo sapiens"

<400> SEQUENCE: 8

Ser Val Glu Thr Ile Lys Glu Asp Met Asn Val Lys Phe Phe Asn Ser
1               5                   10                  15

Asn Lys Lys Lys Arg Asp Asp Phe Glu Lys Leu Thr Asn Tyr Ser Val
            20                  25                  30

Thr Asp Leu Asn Val Gln Arg
        35

<210> SEQ ID NO 9
<211> LENGTH: 25
<212> TYPE: PRT
<213> ORGANISM: Homo sapiens
<220> FEATURE:
<221> NAME/KEY: SOURCE
<222> LOCATION: 1..25
<223> OTHER INFORMATION: /mol_type="protein"
      /organism="Homo sapiens"

<400> SEQUENCE: 9

Val Thr Asp Leu Asn Val Gln Arg Lys Ala Ile His Glu Leu Ile Gln
1               5                   10                  15

Val Met Ala Glu Leu Ser Pro Ala Ala
            20                  25

<210> SEQ ID NO 10
<211> LENGTH: 41
<212> TYPE: PRT
<213> ORGANISM: Homo sapiens
<220> FEATURE:
<221> NAME/KEY: SOURCE
<222> LOCATION: 1..41
<223> OTHER INFORMATION: /mol_type="protein"
      /organism="Homo sapiens"

<400> SEQUENCE: 10

Ser Tyr Ile Leu Ala Phe Gln Leu Cys Ile Val Leu Gly Ser Leu Gly
1               5                   10                  15

Cys Tyr Cys Gln Asp Pro Tyr Val Lys Glu Ala Glu Asn Leu Lys Lys
            20                  25                  30

Tyr Phe Asn Ala Gly His Ser Asp Val
        35                  40
```

```
<210> SEQ ID NO 11
<211> LENGTH: 21
<212> TYPE: PRT
<213> ORGANISM: Homo sapiens
<220> FEATURE:
<221> NAME/KEY: SOURCE
<222> LOCATION: 1..21
<223> OTHER INFORMATION: /mol_type="protein"
      /organism="Homo sapiens"

<400> SEQUENCE: 11

Glu Thr Ile Lys Glu Asp Met Asn Val Lys Phe Phe Asn Ser Asn Lys
1               5                   10                  15

Lys Lys Arg Asp Asp
            20

<210> SEQ ID NO 12
<211> LENGTH: 144
<212> TYPE: PRT
<213> ORGANISM: artificial sequences
<220> FEATURE:
<221> NAME/KEY: SOURCE
<222> LOCATION: 1..144
<223> OTHER INFORMATION: /mol_type="protein"
      /note="recombinant human IFN gamma"
      /organism="artificial sequences"

<400> SEQUENCE: 12

Met Gln Asp Pro Tyr Val Lys Glu Ala Glu Asn Leu Lys Lys Tyr Phe
1               5                   10                  15

Asn Ala Gly His Ser Asp Val Ala Asp Asn Gly Thr Leu Phe Leu Gly
            20                  25                  30

Ile Leu Lys Asn Trp Lys Glu Glu Ser Asp Arg Lys Ile Met Gln Ser
        35                  40                  45

Gln Ile Val Ser Phe Tyr Phe Lys Leu Phe Lys Asn Phe Lys Asp Asp
    50                  55                  60

Gln Ser Ile Gln Lys Ser Val Glu Thr Ile Lys Glu Asp Met Asn Val
65                  70                  75                  80

Lys Phe Phe Asn Ser Asn Lys Lys Lys Arg Asp Asp Phe Glu Lys Leu
                85                  90                  95

Thr Asn Tyr Ser Val Thr Asp Leu Asn Val Gln Arg Lys Ala Ile His
            100                 105                 110

Glu Leu Ile Gln Val Met Ala Glu Leu Ser Pro Ala Ala Lys Thr Gly
        115                 120                 125

Lys Arg Lys Arg Ser Gln Met Leu Phe Gln Gly Arg Arg Ala Ser Gln
    130                 135                 140

<210> SEQ ID NO 13
<211> LENGTH: 144
<212> TYPE: PRT
<213> ORGANISM: artificial sequences
<220> FEATURE:
<221> NAME/KEY: SOURCE
<222> LOCATION: 1..144
<223> OTHER INFORMATION: /mol_type="protein"
      /note="recombinant human IFN gamma"
      /organism="artificial sequences"

<400> SEQUENCE: 13

Met Gln Asp Pro Tyr Val Lys Glu Ala Glu Asn Leu Lys Lys Tyr Phe
1               5                   10                  15

Asn Ala Gly His Ser Asp Val Ala Asp Asn Gly Thr Leu Phe Leu Gly
            20                  25                  30
```

```
Ile Leu Lys Asn Trp Lys Glu Glu Ser Asp Arg Lys Ile Met Gln Ser
         35                  40                  45

Gln Ile Val Ser Phe Tyr Phe Lys Leu Phe Lys Asn Phe Lys Asp Asp
 50                  55                  60

Gln Ser Ile Gln Lys Ser Val Glu Thr Ile Lys Glu Asp Met Asn Val
 65                  70                  75                  80

Lys Phe Phe Asn Ser Asn Lys Lys Arg Asp Asp Phe Glu Lys Leu
                 85                  90                  95

Thr Asn Tyr Ser Val Thr Asp Leu Asn Val Gln Arg Lys Ala Ile His
                100                 105                 110

Glu Leu Ile Gln Val Met Ala Glu Leu Ser Pro Ala Ala Lys Thr Gly
            115                 120                 125

Lys Arg Lys Arg Ser Gln Met Leu Phe Arg Gly Arg Arg Ala Ser Gln
130                 135                 140
```

<210> SEQ ID NO 14
<211> LENGTH: 92
<212> TYPE: PRT
<213> ORGANISM: Bos taurus
<220> FEATURE:
<221> NAME/KEY: SOURCE
<222> LOCATION: 1..92
<223> OTHER INFORMATION: /mol_type="protein"
      /organism="Bos taurus"

<400> SEQUENCE: 14

```
Met Ser Glu Leu Glu Lys Ala Val Val Ala Leu Ile Asp Val Phe His
 1               5                  10                  15

Gln Tyr Ser Gly Arg Glu Gly Asp Lys His Lys Leu Lys Lys Ser Glu
                 20                  25                  30

Leu Lys Glu Leu Ile Asn Asn Glu Leu Ser His Phe Leu Glu Glu Ile
             35                  40                  45

Lys Glu Gln Glu Val Val Asp Lys Val Met Glu Thr Leu Asp Ser Asp
 50                  55                  60

Gly Asp Gly Glu Cys Asp Phe Gln Glu Phe Met Ala Phe Val Ala Met
 65                  70                  75                  80

Ile Thr Thr Ala Cys His Glu Phe Phe Glu His Glu
                 85                  90
```

<210> SEQ ID NO 15
<211> LENGTH: 92
<212> TYPE: PRT
<213> ORGANISM: Homo sapiens
<220> FEATURE:
<221> NAME/KEY: SOURCE
<222> LOCATION: 1..92
<223> OTHER INFORMATION: /mol_type="protein"
      /organism="Homo sapiens"

<400> SEQUENCE: 15

```
Met Ser Glu Leu Glu Lys Ala Met Val Ala Leu Ile Asp Val Phe His
 1               5                  10                  15

Gln Tyr Ser Gly Arg Glu Gly Asp Lys His Lys Leu Lys Lys Ser Glu
                 20                  25                  30

Leu Lys Glu Leu Ile Asn Asn Glu Leu Ser His Phe Leu Glu Glu Ile
             35                  40                  45

Lys Glu Gln Glu Val Val Asp Lys Val Met Glu Thr Leu Asp Asn Asp
 50                  55                  60
```

```
Gly Asp Gly Glu Cys Asp Phe Gln Glu Phe Met Ala Phe Val Ala Met
65                  70                  75                  80

Val Thr Thr Ala Cys His Glu Phe Phe Glu His Glu
                85                  90

<210> SEQ ID NO 16
<211> LENGTH: 94
<212> TYPE: PRT
<213> ORGANISM: Bos taurus
<220> FEATURE:
<221> NAME/KEY: SOURCE
<222> LOCATION: 1..94
<223> OTHER INFORMATION: /mol_type="protein"
      /organism="Bos taurus"

<400> SEQUENCE: 16

Met Gly Ser Glu Leu Glu Thr Ala Met Glu Thr Leu Ile Asn Val Phe
1               5                   10                  15

His Ala His Ser Gly Lys Glu Gly Asp Lys Tyr Lys Leu Ser Lys Lys
                20                  25                  30

Glu Leu Lys Glu Leu Leu Gln Thr Glu Leu Ser Gly Phe Leu Asp Ala
            35                  40                  45

Gln Lys Asp Val Asp Ala Val Asp Lys Val Met Lys Glu Leu Asp Glu
50                  55                  60

Asn Gly Asp Gly Glu Val Asp Phe Gln Glu Tyr Val Val Leu Val Ala
65                  70                  75                  80

Ala Leu Thr Val Ala Cys Asn Asn Phe Phe Trp Glu Asn Ser
                85                  90

<210> SEQ ID NO 17
<211> LENGTH: 94
<212> TYPE: PRT
<213> ORGANISM: Bos taurus
<220> FEATURE:
<221> NAME/KEY: SOURCE
<222> LOCATION: 1..94
<223> OTHER INFORMATION: /mol_type="protein"
      /organism="Bos taurus"

<400> SEQUENCE: 17

Met Gly Ser Glu Leu Glu Thr Ala Met Glu Thr Leu Ile Asn Val Phe
1               5                   10                  15

His Ala His Ser Gly Lys Glu Gly Asp Lys Tyr Lys Leu Ser Lys Lys
                20                  25                  30

Glu Leu Lys Glu Leu Leu Gln Thr Glu Leu Ser Gly Phe Leu Asp Ala
            35                  40                  45

Gln Lys Asp Ala Asp Ala Val Asp Lys Val Met Lys Glu Leu Asp Glu
50                  55                  60

Asn Gly Asp Gly Glu Val Asp Phe Gln Glu Tyr Val Val Leu Val Ala
65                  70                  75                  80

Ala Leu Thr Val Ala Cys Asn Asn Phe Phe Trp Glu Asn Ser
                85                  90
```